United States Patent
Wondka et al.

(10) Patent No.: US 10,058,668 B2
(45) Date of Patent: Aug. 28, 2018

(54) METHODS AND DEVICES FOR SENSING RESPIRATION AND PROVIDING VENTILATION THERAPY

(71) Applicant: BREATHE TECHNOLOGIES, INC., Irvine, CA (US)

(72) Inventors: Anthony Wondka, Thousand Oaks, CA (US); Gregory Kapust, San Ramon, CA (US); Robert Bryan, San Ramon, CA (US); Michael Khenansho, Modesto, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1158 days.

(21) Appl. No.: 14/221,210

(22) Filed: Mar. 20, 2014

(65) Prior Publication Data

US 2014/0288456 A1 Sep. 25, 2014

Related U.S. Application Data

(62) Division of application No. 12/153,423, filed on May 19, 2008, now abandoned.

(Continued)

(51) Int. Cl.
*A61M 16/04* (2006.01)
*A61B 5/00* (2006.01)
(Continued)

(52) U.S. Cl.
CPC ......... *A61M 16/0427* (2014.02); *A61B 5/082* (2013.01); *A61B 5/085* (2013.01);
(Continued)

(58) Field of Classification Search
CPC .. A61M 2016/0015; A61M 2016/0018; A61M 2016/0021; A61M 2016/0027;
(Continued)

(56) References Cited

U.S. PATENT DOCUMENTS

| 50,641 A | 10/1865 | Stone |
|---|---|---|
| 428,592 A | 5/1890 | Chapman |

(Continued)

FOREIGN PATENT DOCUMENTS

| CA | 2535450 | 2/2005 |
|---|---|---|
| CN | 1750854 | 3/2006 |

(Continued)

OTHER PUBLICATIONS

Machine translation of EP 1820527 A1.*

(Continued)

*Primary Examiner* — Jackie Tan-Uyen T Ho
*Assistant Examiner* — Joseph D Boecker
(74) *Attorney, Agent, or Firm* — Stetina Brunda Garred & Brucker

(57) ABSTRACT

Methods and systems are provided for intra-airway breath sensors where intra-airway breath sensors are not located within a ventilation gas delivery circuit, but are exposed to spontaneous respiration airflow from a patient. Furthermore, methods and systems of the present invention may be used to protect an intra-airway breath sensor from contacting tissue or accumulating debris that may impair abilities of the intra-airway breath sensors.

19 Claims, 15 Drawing Sheets

Related U.S. Application Data

(60) Provisional application No. 60/924,514, filed on May 18, 2007.

(51) Int. Cl.

| | | |
|---|---|---|
| *A61B 5/08* | (2006.01) | |
| *A61B 5/085* | (2006.01) | |
| *A61B 5/087* | (2006.01) | |
| *A61B 5/097* | (2006.01) | |
| *A61M 16/00* | (2006.01) | |
| *A61M 16/10* | (2006.01) | |

(52) U.S. Cl.
CPC .......... *A61B 5/0873* (2013.01); *A61B 5/0878* (2013.01); *A61B 5/097* (2013.01); *A61B 5/6853* (2013.01); *A61B 5/6858* (2013.01); *A61M 16/0003* (2014.02); *A61M 16/042* (2014.02); *A61M 16/0434* (2013.01); *A61M 16/0465* (2013.01); *A61M 16/0475* (2014.02); *A61M 16/0486* (2014.02); *A61M 2016/003* (2013.01); *A61M 2016/0021* (2013.01); *A61M 2016/0027* (2013.01); *A61M 2016/0036* (2013.01); *A61M 2016/102* (2013.01); *A61M 2205/332* (2013.01); *A61M 2205/3306* (2013.01); *A61M 2205/3375* (2013.01); *A61M 2230/43* (2013.01); *A61M 2230/65* (2013.01)

(58) Field of Classification Search
CPC .... A61M 2016/003; A61M 2016/0033; A61M 2016/0036; A61M 16/0003; A61M 16/04; A61M 16/0402; A61M 16/042; A61M 16/0427; A61M 16/0463; A61M 16/0434; A61M 16/0465; A61M 16/0475; A61M 16/0486; A61M 2205/3306; A61M 2205/332; A61M 2205/3344; A61M 2205/3375; A61M 2230/43; A61M 2230/65; A61M 16/00; A61M 16/0057; A61B 5/087; A61B 5/097
USPC ........ 128/204.23, 207.14, DIG. 26; 600/532, 600/533, 537, 538, 120–125
See application file for complete search history.

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riu Pla |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,642,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazner |
| 4,263,908 A | 4/1981 | Mizerak |
| 4,265,237 A | 5/1981 | Schwanbom et al. |
| 4,266,540 A | 5/1981 | Panzik et al. |
| 4,270,530 A * | 6/1981 | Baum .................. A61M 16/04 128/204.25 |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum et al. |
| 4,537,188 A | 8/1985 | Phuc |
| 4,539,984 A | 9/1985 | Kiszel et al. |

(56) References Cited

U.S. PATENT DOCUMENTS

| | | |
|---|---|---|
| 4,548,590 A | 10/1985 | Green |
| 4,559,940 A | 12/1985 | McGinnis |
| 4,567,888 A | 2/1986 | Robert |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pastemack |
| 5,080,107 A * | 1/1992 | Teves ............... A61B 7/023 |
| | | 128/207.15 |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,291,882 A | 3/1994 | Makhoul |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Wesffall et al. |
| 5,335,656 A | 8/1994 | Bowe et al. |
| 5,339,809 A | 8/1994 | Beck, Jr. et al. |
| 5,349,946 A | 9/1994 | McComb |
| 5,367,292 A | 11/1994 | Szoke |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,421,325 A * | 6/1995 | Cinberg ............... A61M 16/04 |
| | | 128/200.26 |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes et al. |

(56) References Cited

U.S. PATENT DOCUMENTS

| | | | |
|---|---|---|---|
| 5,509,409 A | 4/1996 | Weatherholt | |
| 5,513,628 A | 5/1996 | Coles et al. | |
| 5,513,631 A | 5/1996 | McWilliams | |
| 5,513,635 A | 5/1996 | Bedi | |
| 5,522,382 A | 6/1996 | Sullivan et al. | |
| 5,526,806 A | 6/1996 | Sansoni | |
| 5,529,060 A | 6/1996 | Salmon et al. | |
| 5,533,506 A | 7/1996 | Wood | |
| 5,535,738 A | 7/1996 | Estes et al. | |
| 5,537,997 A | 7/1996 | Mechlenburg et al. | |
| 5,538,002 A | 7/1996 | Boussignac et al. | |
| 5,542,415 A | 8/1996 | Brody | |
| 5,546,935 A * | 8/1996 | Champeau | A61M 16/04 128/204.23 |
| 5,549,106 A | 8/1996 | Gruenke et al. | |
| 5,551,419 A | 9/1996 | Froehlich et al. | |
| 5,558,086 A | 9/1996 | Smith et al. | |
| 5,564,416 A | 10/1996 | Jones | |
| 5,575,282 A | 11/1996 | Knoch et al. | |
| 5,582,164 A | 12/1996 | Sanders | |
| 5,593,143 A | 1/1997 | Ferrarin | |
| 5,595,174 A | 1/1997 | Gwaltney | |
| 5,598,837 A | 2/1997 | Sirianne, Jr. et al. | |
| 5,598,840 A | 2/1997 | Lund et al. | |
| 5,603,315 A | 2/1997 | Sasso, Jr. | |
| 5,605,148 A | 2/1997 | Jones | |
| 5,626,131 A | 5/1997 | Chua et al. | |
| 5,632,269 A | 5/1997 | Zdrojkowski | |
| 5,636,630 A | 6/1997 | Miller et al. | |
| 5,645,053 A | 7/1997 | Remmers et al. | |
| 5,645,054 A | 7/1997 | Cotner et al. | |
| 5,647,351 A | 7/1997 | Weismann et al. | |
| 5,669,377 A | 9/1997 | Fenn | |
| 5,669,380 A | 9/1997 | Garry et al. | |
| 5,676,132 A | 10/1997 | Tillotson et al. | |
| 5,676,135 A | 10/1997 | McClean | |
| 5,682,878 A | 11/1997 | Ogden | |
| 5,682,881 A | 11/1997 | Winthrop et al. | |
| 5,687,713 A | 11/1997 | Bahr et al. | |
| 5,687,714 A | 11/1997 | Kolobow et al. | |
| 5,687,715 A | 11/1997 | Landis et al. | |
| 5,690,097 A | 11/1997 | Howard et al. | |
| 5,692,497 A | 12/1997 | Schnitzer et al. | |
| 5,697,364 A | 12/1997 | Chua et al. | |
| 5,704,345 A | 1/1998 | Berthon-Jones | |
| 5,711,296 A | 1/1998 | Kolobow | |
| 5,715,812 A | 2/1998 | Deighan et al. | |
| 5,715,815 A | 2/1998 | Lorenzen et al. | |
| 5,720,278 A | 2/1998 | Lachmann et al. | |
| 5,735,268 A | 4/1998 | Chua et al. | |
| 5,735,272 A | 4/1998 | Dillon et al. | |
| 5,740,796 A | 4/1998 | Skog | |
| 5,752,511 A | 5/1998 | Simmons et al. | |
| 5,762,638 A | 6/1998 | Shikani et al. | |
| 5,791,337 A | 8/1998 | Coles et al. | |
| 5,819,723 A | 10/1998 | Joseph | |
| 5,826,579 A | 10/1998 | Remmers et al. | |
| 5,845,636 A | 12/1998 | Gruenke et al. | |
| 5,865,173 A | 2/1999 | Froehlich | |
| 5,865,174 A | 2/1999 | Kloeppel | |
| 5,881,723 A | 3/1999 | Wallace et al. | |
| 5,904,648 A | 5/1999 | Arndt et al. | |
| 5,906,204 A | 5/1999 | Beran et al. | |
| 5,911,756 A | 6/1999 | Debry | |
| 5,915,379 A | 6/1999 | Wallace et al. | |
| 5,915,381 A | 6/1999 | Nord | |
| 5,918,597 A | 7/1999 | Jones et al. | |
| 5,921,238 A | 7/1999 | Bourdon | |
| 5,921,942 A | 7/1999 | Remmers et al. | |
| 5,921,952 A | 7/1999 | Desmond, III et al. | |
| 5,927,276 A | 7/1999 | Rodriguez | |
| 5,928,189 A | 7/1999 | Phillips et al. | |
| 5,931,160 A | 8/1999 | Gilmore et al. | |
| 5,931,162 A | 8/1999 | Christian | |
| 5,937,853 A | 8/1999 | Strom | |
| 5,937,855 A | 8/1999 | Zdrojkowski et al. | |
| 5,938,118 A | 8/1999 | Cooper | |
| 5,954,050 A | 9/1999 | Christopher | |
| 5,957,136 A | 9/1999 | Magidson et al. | |
| 5,964,223 A | 10/1999 | Baran | |
| 5,975,077 A | 11/1999 | Hofstetter et al. | |
| 5,975,081 A | 11/1999 | Hood et al. | |
| 5,979,440 A | 11/1999 | Honkonen et al. | |
| 5,989,193 A | 11/1999 | Sullivan | |
| 6,000,396 A | 12/1999 | Melker et al. | |
| 6,019,101 A | 2/2000 | Cotner et al. | |
| 6,039,696 A | 3/2000 | Bell | |
| 6,050,260 A | 4/2000 | Daniell et al. | |
| 6,076,519 A | 6/2000 | Johnson | |
| 6,085,747 A | 7/2000 | Axe et al. | |
| 6,091,973 A | 7/2000 | Colla et al. | |
| 6,105,575 A | 8/2000 | Estes et al. | |
| 6,109,264 A | 8/2000 | Sauer | |
| 6,112,746 A | 9/2000 | Kwok et al. | |
| 6,119,694 A | 9/2000 | Correa et al. | |
| 6,120,460 A | 9/2000 | Abreu | |
| 6,123,668 A | 9/2000 | Abreu | |
| 6,131,571 A | 10/2000 | Lampotang et al. | |
| 6,135,970 A | 10/2000 | Kadhiresan et al. | |
| 6,152,132 A | 11/2000 | Psaros | |
| 6,152,134 A | 11/2000 | Webber et al. | |
| 6,158,432 A | 12/2000 | Biondi et al. | |
| 6,192,883 B1 | 2/2001 | Miller, Jr. | |
| 6,203,502 B1 | 3/2001 | Hilgendorf et al. | |
| 6,213,119 B1 | 4/2001 | Brydon et al. | |
| 6,213,955 B1 | 4/2001 | Karakasoglu et al. | |
| 6,220,244 B1 | 4/2001 | McLaughlin | |
| 6,224,560 B1 | 5/2001 | Gazula et al. | |
| 6,227,200 B1 | 5/2001 | Crump et al. | |
| 6,247,470 B1 | 6/2001 | Ketchedjian | |
| 6,269,811 B1 | 8/2001 | Duff et al. | |
| 6,269,812 B1 | 8/2001 | Wallace et al. | |
| 6,273,589 B1 | 8/2001 | Remmers et al. | |
| 6,286,508 B1 | 9/2001 | Remmers et al. | |
| D449,376 S | 10/2001 | McDonald et al. | |
| D449,883 S | 10/2001 | McDonald et al. | |
| 6,298,850 B1 | 10/2001 | Argraves | |
| 6,305,374 B1 | 10/2001 | Zdrojkowski et al. | |
| 6,314,957 B1 | 11/2001 | Boissin et al. | |
| 6,315,739 B1 | 11/2001 | Merilainen et al. | |
| D451,598 S | 12/2001 | McDonald et al. | |
| 6,328,038 B1 | 12/2001 | Kessler et al. | |
| 6,328,753 B1 | 12/2001 | Zammit | |
| 6,332,463 B1 | 12/2001 | Farrugia et al. | |
| 6,345,619 B1 | 2/2002 | Finn | |
| 6,349,720 B1 * | 2/2002 | Clark | A61M 16/04 128/200.26 |
| 6,357,438 B1 | 3/2002 | Hansen | |
| 6,357,440 B1 | 3/2002 | Hansen et al. | |
| 6,360,741 B2 | 3/2002 | Truschel | |
| 6,360,745 B1 | 3/2002 | Wallace et al. | |
| 6,363,933 B1 | 4/2002 | Berthon-Jones | |
| 6,367,474 B1 | 4/2002 | Berthon-Jones et al. | |
| 6,369,838 B1 | 4/2002 | Wallace et al. | |
| 6,371,114 B1 | 4/2002 | Schmidt et al. | |
| 6,378,520 B1 | 4/2002 | Davenport | |
| 6,390,091 B1 | 5/2002 | Banner et al. | |
| 6,394,088 B1 | 5/2002 | Frye et al. | |
| 6,398,739 B1 | 6/2002 | Sullivan et al. | |
| 6,418,928 B1 | 7/2002 | Bordewick et al. | |
| 6,422,240 B1 | 7/2002 | Levitsky et al. | |
| 6,423,001 B1 | 7/2002 | Abreu | |
| 6,427,690 B1 | 8/2002 | McCombs et al. | |
| 6,431,172 B1 | 8/2002 | Bordewick | |
| 6,439,228 B1 | 8/2002 | Hete et al. | |
| 6,439,229 B1 | 8/2002 | Du et al. | |
| 6,439,234 B1 | 8/2002 | Curti et al. | |
| 6,439,235 B1 | 8/2002 | Larquet et al. | |
| 6,450,164 B1 | 9/2002 | Banner et al. | |
| 6,450,166 B1 | 9/2002 | McDonald et al. | |
| 6,457,472 B1 | 10/2002 | Schwartz et al. | |
| 6,467,477 B1 | 10/2002 | Frank et al. | |
| 6,478,026 B1 | 11/2002 | Wood | |
| 6,494,202 B2 | 12/2002 | Farmer | |

(56) References Cited

U.S. PATENT DOCUMENTS

| | | |
|---|---|---|
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,668,829 B2 | 2/2003 | Biondi et al. |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,166 B2 | 6/2003 | Boussignac |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,640,806 B2 | 7/2003 | Yurko |
| 6,609,517 B1 | 8/2003 | Estes et al. |
| 6,629,529 B2 | 8/2003 | Arnott |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,631,919 B1 | 10/2003 | West et al. |
| 6,634,356 B1 | 10/2003 | O'Dea et al. |
| 6,635,021 B1 | 10/2003 | Sullivan et al. |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,669,712 B2 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,823,866 B2 | 6/2004 | Jafari et al. |
| 6,758,217 B1 | 7/2004 | Younes et al. |
| 6,761,172 B2 | 7/2004 | Boussignac |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,915,803 B2 | 1/2005 | Berthon-Jones et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St Goar et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenbrug et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |

(56) References Cited

U.S. PATENT DOCUMENTS

| | | |
|---|---|---|
| 7,195,016 B2 | 3/2007 | Loyd et al. |
| 7,195,018 B1 | 3/2007 | Goldstein |
| 7,201,169 B2 | 4/2007 | Wikie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,416,532 B1 * | 8/2008 | Broshears ............... A61B 5/01 600/549 |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkel |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 8,393,328 B2 * | 3/2013 | Angel ................... A61M 16/04 128/200.26 |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |

(56) References Cited

U.S. PATENT DOCUMENTS

| | | |
|---|---|---|
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005936 A1 | 1/2005 | Wondka |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034721 A1* | 2/2005 | Freitag ............... A61M 16/0072 128/200.24 |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2005/0279360 A1* | 12/2005 | Wei ....................... A61M 16/04 128/207.14 |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovithc |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Lobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0264772 A1 | 11/2006 | Aljuri et al. |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0144526 A1* | 6/2007 | Blom ................. A61M 16/0468 128/207.16 |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunarathnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |

(56) References Cited

U.S. PATENT DOCUMENTS

| | | |
|---|---|---|
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunarathnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241651 A1 | 10/2009 | Jafari et al. |
| 2009/0241947 A1 | 10/2009 | Bedini et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Selver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunarathnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunarathnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Blussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| CN | 200480029872 | 11/2006 |
| DE | 19626924 | 1/1998 |
| DE | 29902267 U1 | 7/1999 |
| DE | 19841070 | 5/2000 |
| DE | 19849571 | 5/2000 |
| DE | 10337138 | 8/2003 |
| DE | 10337138.9 | 3/2005 |
| DE | 102006023637.8 | 11/2007 |
| EP | 0125424 | 11/1984 |
| EP | 0692273 | 1/1996 |
| EP | 0778035 | 6/1997 |

(56) References Cited

FOREIGN PATENT DOCUMENTS

| | | | | |
|---|---|---|---|---|
| EP | 1359961 | 11/2003 | | |
| EP | 1654023 | 5/2006 | | |
| EP | 1820527 A1 * | 8/2007 | ............ | A61B 1/267 |
| EP | 2377462 | 11/2010 | | |
| GB | 2174609 | 11/1986 | | |
| GB | 2201098 | 8/1988 | | |
| GB | 1055148 | 6/1989 | | |
| GB | 2338420 | 12/1999 | | |
| JP | S63-57060 | 3/1998 | | |
| JP | 2002-204830 | 7/2002 | | |
| JP | 2006-522883 | 2/2007 | | |
| WO | WO-1992/11054 | 7/1992 | | |
| WO | 9745153 | 12/1997 | | |
| WO | WO-98/01176 | 1/1998 | | |
| WO | WO-1998/01176 | 1/1998 | | |
| WO | WO-1999/04841 | 2/1999 | | |
| WO | WO 9965552 A1 * | 12/1999 | ............ | A61M 16/04 |
| WO | WO-2009/109005 | 9/2000 | | |
| WO | WO-2009/115944 | 9/2000 | | |
| WO | WO-2000/064521 | 11/2000 | | |
| WO | WO-2006/138580 | 12/2000 | | |
| WO | WO-01/076655 | 10/2001 | | |
| WO | WO-2001/076655 | 10/2001 | | |
| WO | WO-2002/062413 | 8/2002 | | |
| WO | WO-2004/009169 | 1/2004 | | |
| WO | WO-2005/014091 | 2/2005 | | |
| WO | WO2005014091 | 2/2005 | | |
| WO | WO-2005/018524 | 3/2005 | | |
| WO | WO-2005/086943 | 9/2005 | | |
| WO | WO-2007/035804 | 3/2007 | | |
| WO | WO2007035804 | 3/2007 | | |
| WO | WO-2007/139531 | 12/2007 | | |
| WO | WO-2007142812 | 12/2007 | | |
| WO | WO2007142812 | 12/2007 | | |
| WO | WO-2008/014543 | 2/2008 | | |
| WO | WO-2008/019102 | 2/2008 | | |
| WO | WO-2008/052534 | 5/2008 | | |
| WO | WO-2008/112474 | 9/2008 | | |
| WO | WO-2008/138040 | 11/2008 | | |
| WO | WO-2008/144589 | 11/2008 | | |
| WO | WO-2008/144669 | 11/2008 | | |
| WO | WO-2009/042973 | 4/2009 | | |
| WO | WO-2009/042974 | 4/2009 | | |
| WO | WO-2009/059353 | 5/2009 | | |
| WO | WO-2009/064202 | 5/2009 | | |
| WO | WO-2009/074160 | 6/2009 | | |
| WO | WO-2009/082295 | 7/2009 | | |
| WO | WO-2009/087607 | 7/2009 | | |
| WO | WO-2009/092057 | 7/2009 | | |
| WO | WO-2009/103288 | 8/2009 | | |
| WO | WO-2009/115948 | 9/2009 | | |
| WO | WO-2009/115949 | 9/2009 | | |
| WO | WO-2009/129506 | 10/2009 | | |
| WO | WO-2009/136101 | 11/2009 | | |
| WO | WO-2009/139647 | 11/2009 | | |
| WO | WO-2009/149351 | 12/2009 | | |
| WO | WO-2009/149353 | 12/2009 | | |
| WO | WO-2009/149355 | 12/2009 | | |
| WO | WO-2009/149357 | 12/2009 | | |
| WO | WO-2009/151344 | 12/2009 | | |
| WO | WO-2009/151791 | 12/2009 | | |
| WO | WO-2010/000135 | 1/2010 | | |
| WO | WO-2010/021556 | 2/2010 | | |
| WO | WO-2010/022363 | 2/2010 | | |
| WO | WO-2010/039989 | 4/2010 | | |
| WO | WO-2010/041966 | 4/2010 | | |
| WO | WO-2010/044034 | 4/2010 | | |
| WO | WO-2010/057268 | 5/2010 | | |
| WO | WO-2010/059049 | 5/2010 | | |
| WO | WO-2010/060422 | 6/2010 | | |
| WO | WO-2010/068356 | 6/2010 | | |
| WO | WO-2010/070493 | 6/2010 | | |
| WO | WO-2010/070497 | 6/2010 | | |
| WO | WO-2010/070498 | 6/2010 | | |
| WO | WO-2010/076711 | 7/2010 | | |
| WO | WO-2010/081223 | 7/2010 | | |
| WO | WO-2010/091157 | 8/2010 | | |
| WO | WO-2010/099375 | 9/2010 | | |
| WO | WO-2010/102094 | 9/2010 | | |
| WO | WO-2010/115166 | 10/2010 | | |
| WO | WO-2010/115168 | 10/2010 | | |
| WO | WO-2010/115169 | 10/2010 | | |
| WO | WO-2010/115170 | 10/2010 | | |
| WO | WO-2010/116275 | 10/2010 | | |
| WO | WO-2010/132853 | 11/2010 | | |
| WO | WO-2010/136923 | 12/2010 | | |
| WO | WO-2010/139014 | 12/2010 | | |
| WO | WO-2010/150187 | 12/2010 | | |
| WO | WO-2011/002608 | 1/2011 | | |
| WO | WO-2011/004274 | 1/2011 | | |
| WO | WO-2011/006184 | 1/2011 | | |
| WO | WO-2011/006199 | 1/2011 | | |
| WO | WO-2011/014931 | 2/2011 | | |
| WO | WO-2011/017033 | 2/2011 | | |
| WO | WO-2011/017738 | 2/2011 | | |
| WO | WO-2011/021978 | 2/2011 | | |
| WO | WO-2011/022779 | 3/2011 | | |
| WO | WO-2011/024383 | 3/2011 | | |
| WO | WO-2011/029073 | 3/2011 | | |
| WO | WO-2011/029074 | 3/2011 | | |
| WO | WO2011035373 | 3/2011 | | |
| WO | WO2011038950 | 4/2011 | | |
| WO | WO2011038951 | 4/2011 | | |
| WO | WO2011044627 | 4/2011 | | |
| WO | WO2011057362 | 5/2011 | | |
| WO | WO2011059346 | 5/2011 | | |
| WO | WO2011061648 | 5/2011 | | |
| WO | WO2011062510 | 5/2011 | | |
| WO | WO2011086437 | 7/2011 | | |
| WO | WO2011086438 | 7/2011 | | |
| WO | WO2011112807 | 9/2011 | | |

OTHER PUBLICATIONS

Extended European Search Report for European Patent Application No. 08755904.3 dated Sep. 7, 2015.
Canadian Office Action for Canadian Patent Application No. 2,688,719; dated Feb. 23, 2015.
International Search Report and Opinion for Application No. PCT/US07/17400, dated Apr. 28, 2008.
European Search Reoprt dated Oct. 19, 2007 EP 04762494.
International Search Report for wo2005/014091 (Application No. PCT/DE04/1646), dated Jan. 17, 2005.
International Search Report and Written Opinion for PCT/US07/12108, dated Aug. 8, 2008.
Christopher et al., "Transtracheal Oxygen Therapy for Refractory Hypoxemia," JAMA 1986, vol. 256, No. 4, pp. 494-497.
Teip et al., "Pulsed nasal and transtracheal oxygen delivery," Chest, 1990, vol. 97, pp. 364-368.
Yaeger et al., "Oxygen Therapy Using Pulse and Continuous Flow with a Transtracheal catheter and a nasal Cannula," Chest, 1994, vol. 106, pp. 854-860.
Christopher et al., "Preliminary Observations of Transtracheal Augmented Ventilation for Chronic Severe Respiratory Disease," Respiratory Care, Jan. 2001, vol. 46, No. 1, pp. 15-25.
Fink, J.B., "Helium-Oxygen: An Old Therapy Creates New Interest," J Resp Care Pract now RT for Decision Makers in Respiratory Care, Apr./May 1999, pp. 71-76.
Haenel et al., "Efficacy of Selective Intrabronchial Air Insufflation in Acute Lobar Colapse," AmJ Surg, 1992, vol. 164, No. 5, pp. 501-505.
AARC Clinical Practice Guideline: Oxygen Therapy in the Home or Extended Care Facility, Respiratory Care, Aug. 1992, vol. 37, No. 8, pp. 918-922.
McIntyre, N. R., "Long-Term Oxygen Therapy: Conference Summary," Respiratory Care, Feb. 2000, vol. 45, No. 2, pp. 237-245.
VHA/DOD Clinical Practice Guideline, "Management of Chronic Obstructive Pulmonary Disease," Ver. 1.1a, Aug. 1999, Updated Nov. 1999.

(56) References Cited

OTHER PUBLICATIONS

Blanch, L. L., "Clinical Studies of Tracheal Gas Insufflation," Respiratory Care, Feb. 2001, vol. 46, No. 2, pp. 158-166.
Gregoretti et al., "Transtracheal Open Ventilation in Acute Respiratory Failure Secondary to Severe Chronic Obstructive Pulmonary Disease Exacerbation," Am J Respir Cit Care Med. 2006, vol. 173, No. 8, pp. 877-881.
Chang et al., "Reduced Inspiratory Muscle endurance Following Successful Weaning from Prolonged Mechanical Ventilation," Chest, 2005, vol. 128, No. 2, pp. 553-559.
Gaughan et al., "A comparison in a Lung Model of Low-and-High-Flow Regulators for Transtracheal Jet Ventilation," Anesthesiology, 1992, vol. 77, No. 1, pp. 189-199.
Menon et al., "Tracheal Perforation. A Complication Associated with Transtracheal Oxygen Therapy," Chest, 1993, vol. 140, No. 2, pp. 636-637.
Rothe, et al. "Near Fatal Complication of Transtracheal Oxygen Therapy with the Scoop(r) System," Pneumologie, 1996, vol. 50, No. 10, pp. 700-702 (English Abstract provided).
Ambrosino, "Weaning and Respiratory Muscle Dysfunction: The Egg Chicken Dilemma," Chest, 2005, vol. 128(2), pp. 481-483.
Messinger et al., "Using Tracheal Pressure to Trigger the Ventilator and Control Airway Pressure During Continuous Positive Airway Pressure Decreases Work of Breathing," Chest, 1995, vol. 108, No. 2, pp. 509-514.
Prigent et al., "Comparative Effects of Two Ventilatory Modes on Speech in Tracheostomized Patients with Neuromuscular Disease," Am J Respir Crit Care Med. 2003, vol. 167, No. 8, pp. 114-119.
Koska et al., "Evaluatioin of a fiberoptic system for airway pressure monitory," J. Clin Monit, 1993, vol. 10, No. 4, pp. 247-250.
Banner et al., "Imposed work of breathing and methods of triggering demand-flow, continuous positive airway pressure system," Critical Care Medicine, 1993, vol. 21, No. 2, pp. 183-190.
Banner et al., "Site of pressure measurement during spontaneous breathing with continuous positive airway pressure: Effect on calculating imposed work of breathing," Critical Care, 1992, vol. 20, No. 4, pp. 528-533.
Sinderby et al., "Neural control of mechanical ventilation in respiratory failure" Nat Med., 1999; 5:1433-1436.
Passy-Muir Inc., "Clinical Inservice Outline", Apr. 2004, 19 pages.
Charlotte Regional Medical Center, "Application of the Passy-Muir Tracheostomy and Ventilator", Speech-Language Pathology Department, Jan. 1995, 8 pages.
"Passy-Muir Speaking Valves," Respiratory, Nov. 13, 1998, 7 pages.
Porta et al., "Mask proportional assist vs pressure support ventilation in patients in clinically stable condition with chronic venilatory failure," Chest, 2002: 122(2), pp. 479-488.
Prigent et al., "Comparative effects of two ventilatory modes on speech in tracheostomized patients with neuromuscular disease," Am. J. Resp. Crit. Care Med., 2003: 167(8), pp. 114-119.
Puente-Maestu et al., "Dyspnea, ventilatory pattern, and changes in dyamic hyperinflation related to the intensity of constant work rate exercise in COPD," Chest, 2005: 128(2), pp. 651-656.
Ram et al., "Non-invasive positive pressure ventilation for treatment of respiratory failure due to exacerbations of chronic obstructive pulmonary disease," Cochrane Database Syst Rev., 2004(3): 1-72.
Rothe et al., "Near fatal complication of transtracheal oxygen therapy with the SCOOP(R) system," Pneumologie, 1996: 50(10), pp. 700-702.
Rothfleisch et al., Facillation of ftheroptic nasotracheal intubation in a morbidly obese patient by simuntaneous use of nasal CPAP, Chest, 1994 106(1): 287-288.
Sanders et al., "CPAP via nasal mask: A treatment for occlusive sleep apnea," Chest, 1983: 839!), pp. 144-145.
Sinderby et al., "Neural control of mechanical ventilation in respiratory failure, " Nat. Med., 1999: 5(12), pp. 1433-1436.
Somfayet al., "Dose-Response effect of oxygen on hyperinflation and exercise endurance in nonhypoxaemic COPD patients," Eur. Resp. J., 2001: 18, pp. 77-84.
Sullivan et al., "Reversal of obstructive sleep apnoea by continuous positive airway pressure applied through the nares," The Lancet, 1981: 1(8225), pp. 862-865.
Sullivan, "Home treatment of obstructive sleep apnoea with continuous positive airway pressure applied through a nose-mask," Bull Eur Physiopathol Respir., 1984: 20(1), pp. 49-54.
Tiep et al., "Pulsed nasal and transtracheal oxygen delivery," Chest, 1990: 97, pp. 364-368.
Tsubol et al., "Ventilatory support during exercise in patients with pulmonary tuberculosis seqelae," Chest, 1997: 112(4), pp. 1000-1007.
VHA/DOD Clinical Practice Guideline, "Management of chronic obstructive pulmonary disease," Aug. 1999, Ver. 1.1a, Updated Nov. 1999.
Wijkstra et al., "Nocturnal non-invasive positive pressure ventilation for stable chronic ostructive pulmonary disease," Cochrane Database Syst. Rev., 2002, 3: 1-22.
Yaeger et al., "Oxygen therapy using pulse and continuous flow with a transtracheal catheter and a nasal cannula," Chest, 1994: 106, pp. 854-860.
Walsh, "McGraw Hill pocket reference machinists' and metalworker pocket reference," New York McGraw-Hill, 2000, pp. 3-67, submitting 3 pages.
International preliminary report and written opinion on patentabiility for PCT/DE2004/001646, dated Jul. 3, 2006.
European patent office search report dated Oct. 19, 2007 in co-penidng EP04762494.
International preliminary report and written opinion on patentablilty for PCT/US04/26800 dated Jun. 22, 2006.
International preliminary report and written opinion on patentablilty for PCT/US07/12108, dated Aug. 8, 2008.
International preliminary report and written opinion on patentablilty for PCT/US07/17400, dated Apr. 28, 2008.
International preliminary report and written opinion on patentablilty for PCT/US08/64015, dated Sep. 26, 2008.
International preliminary report and written opinion on patentablilty for PCT/US08/64164, dated Sep. 29, 2008.
International preliminary report and written opinion on patentablilty for PCT/US08//8031, dated Nov. 24, 2008.
International preliminary report and written opinion on patentablilty for PCT/US08/78033, dated Dec. 3, 2008.
International preliminary report and written opinion on patentablilty for PCT/US09/054673, dated Oct. 8, 2009.
International preliminary report and written opinion on patentablilty for PCT/US09/41027, dated Dec. 14, 2009.
International preliminary report and written opinion on patentability for PCT/US09/59272, dated Dec. 2, 2009.
International preliminary report and written opinion on patentability for PCT/US2006/036600, dated Apr. 3, 2007.
International preliminary report and written opinion on patentability for PCT/US2009/031355 dated Mar. 11, 2009.
International preliminary report and written opinion on patentability for PCT/US2009/041034, dated Jun. 10, 2009.
International preliminary report and written opinion on patentability for PCT/US2010/029871, dated Jul. 12, 2010.
International preliminary report and written opinion on patentability for PCT/US2010/029873, dated Jun. 28, 2010.
International preliminary report and written opinion on patentability for PCT/US2010/029874, dated Jul. 12, 2010.
International preliminary report and written opinion on patentability for PCT/US/2010/029875, dated Jul. 12, 2010.
International preliminary report and written opinion on patentablilty for PCT/US2010/047920, dated Nov. 1, 2010.
International preliminary report and written opinion on patentablilty for PCT/US2010/047921, dated Jan. 27, 2011.
International search report for PCT/De2004/001646, dated Jan. 17, 2005.
In the U.S. Patent and Trademark Office, Supplemental Notice of Allowance dated in re: U.S. Appl. No. 10/771,803, dated Dec. 2, 2008, 2 pages.
In the U.S. Patent and Trademark Office, Supplemental Notice of Allowance dated in re: U.S. Appl. No. 10/771,803, dated Nov. 7, 2008, 2 pages.

(56) References Cited

OTHER PUBLICATIONS

In the U.S. Patent and Trademark Office, Examiner's Interview Summary in re: U.S. Appl. No. 10/771,803, dated Oct. 31, 2008, 4 pages.
In the U.S. Patent and Trademark Office, Supplemental Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14. 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Non Final Office Action re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance dated in re: U.S. Appl. No. 11/798,965, dated Aug. 21, 2009, 4 pages.
In the U.S. Patent and Trademark Office, Notice of Allowance dated in re: U.S. Appl. No. 11/798,965, dated Jul. 17, 2009, 5 pages.
In the U.S. Patent and Trademark Office, Final Office Action re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance dated in re: U.S. Appl. No. 10/870,849, dated Jun. 16, 2009, 2 pages.
In the U.S. Patent and Trademark Office, Notice of Allowance dated in re: U.S. Appl. No. 10/870,849, dated Jun. 3, 2009, 4 pages.
In the U.S. Patent and Trademark Office, Notice of Allowance dated in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/4153,423, dated Oct. 6, 2011, 8 pages.
In the U.S. Patent and Trademark Office, Notice of Allowance dated in re: U.S. Appl. No. 10/922,054, dated Feb. 12, 2008, 6 pages.
In the U.S. Patent and Trademark Office, Final Office Action re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance dated in re: U.S. Appl. No. 12/076,062, dated Nov. 2, 2011, 7 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," Resp. Care, 1992, 37(8), pp. 918-922.
"ATS Statement: Guidelines for the Six-Minute Walk Test," Am. J. Respir. Crit. Care Med., 2002., 166, pp. 111-117.
Ambrosino, "Exercise and noninvasive ventilatory support," Monaldi Arch Chest Dis., 2000, 55(3), pp. 242-246.
Ambrosino, "Weaning and Respiratory Muscle Dysfunction: The Egg Chicken Dilemma," Chest, 2005: 128(2), pp. 481-483.
Bach et al., "Intermittent Positive Pressure Ventilation via Nasal Access in the Management of Respiratory Insufficiency," Chest, 1987: 92(1), pp. 168-170.
Banner et al., "Extubating at a Pressure Support Ventilation Level Corresponding to Zero Imposed Work of Breathing," Anesthesiology, Sep. 1994: 81(3A), pp. A271.
Banner et al., "Imposed Work of Breathing and Methods of Triggering a Demand-Flow, Continuous Positive Airway Pressure System," Critical Care Medicine, 1993: 21(2), pp. 183-190.
Banner et al., "Site of Pressure Measurement During Spontaneous Breathing with Continuous Positive Airway Pressure: Effect on Calculating Imposed Work of Breathing." Critical Care Medicine, 1992: 20(4), pp. 528-533.
Barakat et al., "Effect of noninvasive ventilatory support during exercise of a program in pulmonary rehabilitation in patients with COPD," Int. J. Chron. Obstruct. Pulmon. Dis., 2007: 2(4), pp. 585-591.
Barreiro et al., Noninvasive ventilation, Crit Care Clin., 2007: 23(2): 201-22.
Bauer et al., "ADAM nasal CPAP Circuit Adaptation: A Case Report," Sleep, 1991: 14(3), pp. 272-273.
Blanch, "Clinical Studies of Tracheal Gas Insufflation," Resp. Care, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," Monatsschr Kinderheilkd, 1975: 123(4), pp. 141-146.
Boussarsar et al., "Relationship between ventilatory settings and barotrauma in the acute respiratory distress syndrome," Intensive Care Med., 2002: 28(4), 406-13.
Chang et al., "Reduced Inspiratory muscle Endurance Following Successful Weaning From Prolonged Mechanical Ventilation," Chest, 2005: 128(2), pp. 553-559.
Charlotte Regional Mediacl Center, "Application of the Passy-Muir Tracheostomy and Ventilator," Speech-Language Pathology Department, Jan. 1995, 8 pages.
Christopher et al., "Preliminary Observations of Transtracheal Augmented Ventilation for Chronic Severe Respiratory Disease," Resp. Care, 2001: 46(1), pp. 15-25.
Christopher, et al. "Transtracheal Oxygen Therapy for Refractory Hypoxemia," JAMA, 1986: 256(4), pp. 494-497.
Ciccolella et al.; "Administration of High-Flow, Vapor-phased, Humidified Nasal Cannula Air (HF-HNC) Decreases Work of

(56) References Cited

OTHER PUBLICATIONS

Breathing (WOB) in Healthy Subjects During Exercise," AmJRCCM, Apr. 2001: 163(5), Part 2, pp. A622. (Abstract Only).
Clini et al., The Italian multicentre study on noninvasive ventilation in chronic obstructive pulmonary disease patients, Eur. Respir. J., 2002, 20(3): 529-538.
Costa et al., "Influence of noninvasive ventilation by BiPAP on exercise tolerance and respiratory muscle strength in chronic obstructive pulmonary disease patients (COPD)," Rev. Lat. Am. Enfermagem., 2006: 14(3), pp. 378-382.
Diaz et al., "Breathing Pattern and Gas Exchange at Peak Exercise in COPD Patients with and without Tidal Flow Limitation at Rest," European Respiratory Journal, 2001: 17, pp. 1120-1127.
Enright, "The six-minute walk test," Resp. Care, 2003: 8, pp. 783-785.
Ferreira et al., "Trigger Performance of Mid-level ICU Mechanical Ventilators During Assisted Ventilation: A Bench Study," Intensive Care Medicine, 2008, 34: 1669-1675.
Fink, "Helium-Oxygen: An Old Therapy Creates New Interest," J. Resp. Care. Pract. now RT for Decision Makers in Respiratory Care, 1999, pp. 71-76.
Gaughan et al. "A Comparison in a Lung Model of Low-and High-Flow Regulators for Transtracheal Jet Ventilation," Anesthesiology, 1992: 77(1), pp. 189-199.
Gregoretti, et al., "Transtracheal Open Ventilation in Acute Respiratory Failure Secondary to Severe Chronic Obstructive Pulmonary Disease Exacerbation," Am. J. Resp. Crit. Car. Med., 2006: 173(8), pp. 877-881.
Haenel et al., "Efficacy of Selective Intrabronchial Air Insufflation in Acute Lobar Colapse," Am. J. Surg., 1992: 164(5), pp. 501-505.
Keilty et al., "Effect of inspiratory pressure support on exercise tolerance and breathlessness in patients with severe stable chronic obstructive pulmonary disease," Thorax, 1994, 49(10): 990-994.
Kohnlein et al., "Noninvasive ventilation in pulmonary rehabilitation of COPD patients," Respir. Med., 2009, 103: 1329-1336.
Koska et al. "Evaluation of a Fiberopic System for Airway Pressure Monitoring," J. Clin. Monit., 1993: 10(4), pp. 247-250.
Lewis, "Breathless No More, Defeating Adult Sleep Apnea," FDA Consumer Magazine, Jun. 1992, pp. 33-37.
Limberg et al., "Changes in Supplemental Oxygen Prescription in Pulmonary Rehabilitation," Resp. Care, 2006: 51(11), p. 1302.
MacIntyre,"Long-Term Oxygen Therapy; Conference Summary," Resp. Care, 2000: 45(2), pp. 237-245.
MacIntyre et al., "Acute exacerbations and respiratory failure in chronic obstructive pulmonary disease, " Proc. Am. Thorac. Soc., 5(4), pp. 530-535.
Massie et al., "Clinical Outcomes Related to Interface Type in Patients with Obstructive Sleep Apnea/Hypopnea Syndrome Who are Using Continuous Positive Airway Pressure," Chest, 2003: 123(4), pp. 1112-1118.
McCoy, "Oxygen Conservation Techniques and Devices," Resp. Care, 2000: 45(1), pp. 95-104.
McGinley, " A nasal cannula can be used to treat obstructive sleep apnea"; Am. J. Resp. Grit. Care Med., 2007: 176(2) pp. 194-200.
Menadue et al., "Non-invasive ventilation during arm exercise and ground walking in patients with chronic hypercapric respiratory failure," Respirology, 2009, 14(2): 251-259.
Menon et al., "Tracheal Perforation. A Complication Associated with Transtracheal Oxygen therapy," Chest, 1993: 104(2), pp. 636-637.
Messinger et al., "Tracheal Pressure Triggering a Demand-Flow CPAP System Decreases Work of Breathing," Anesthesiology, 1994: 81(3A) p. A272.
Mettey, "Use of CPAP Nasal Cannula for Aids of the Newborns in Tropical Countries," Medecine Tropicale, 1985: 45(1), pp. 87-90.
Nahmias et al., "Treatment of the Obstructive Sleep Apnea Syndrome Using a Nasopharyngeal Tube", Chest, 1988: 94(6), pp. 1142-1147.
Nava et al., "Non-invasive ventilation," Minerva Anestesiol., 2009: 75(1-2), pp. 31-36.
Peters et al., "Combined Physiological Effects of Bronchodilators and Hyperoxia on Exertional Dyspnea in Normoxic COPD," Thorax, 2006: 61, pp. 559-567.
Polkey et al., "Inspiratory pressure support reduces slowing of inspiratory muscle relations rate during exhaustive treadmill walking in sever COPD," Am. J. Resp. Crit. Care Med., 1996: 154(4,10), pp. 1146-1150.
Examination Report for Indian Patent Application No. 7348/CHENP/2009, dated Nov. 24, 2017.

\* cited by examiner

PRIOR ART
FIG. 1A
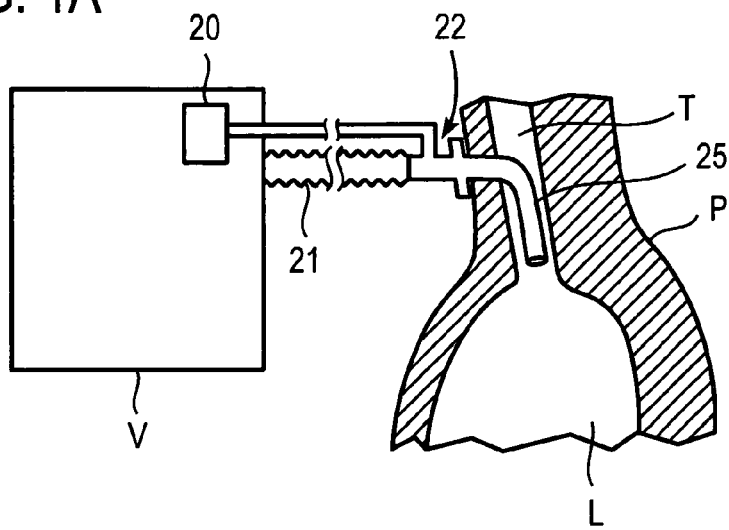
PRIOR ART
FIG. 1B
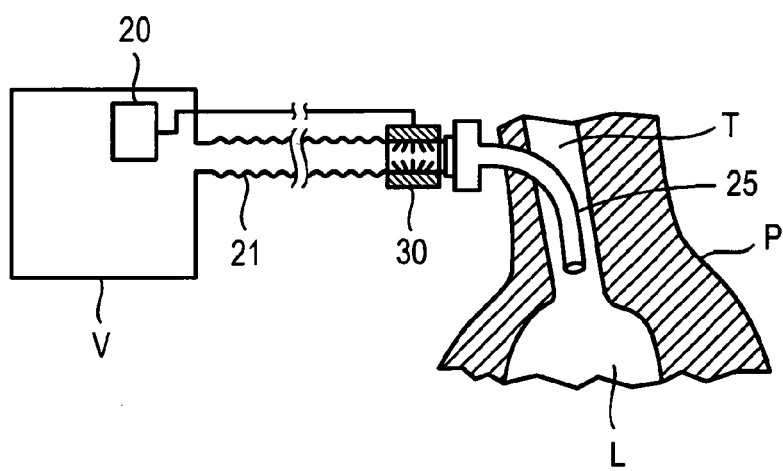
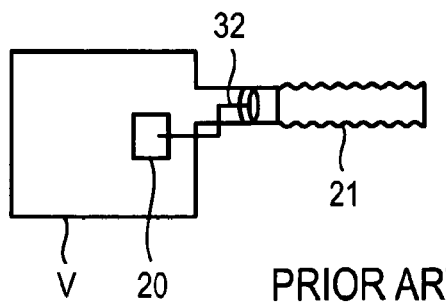
PRIOR ART
FIG. 1C

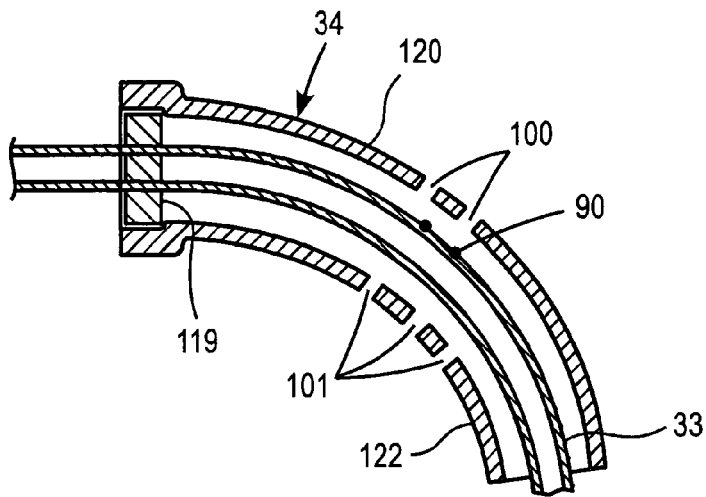
FIG. 16
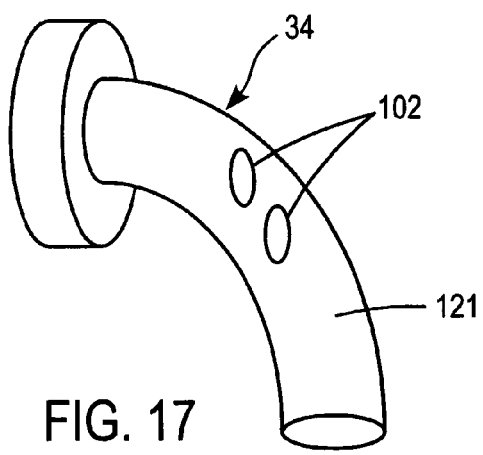
FIG. 17
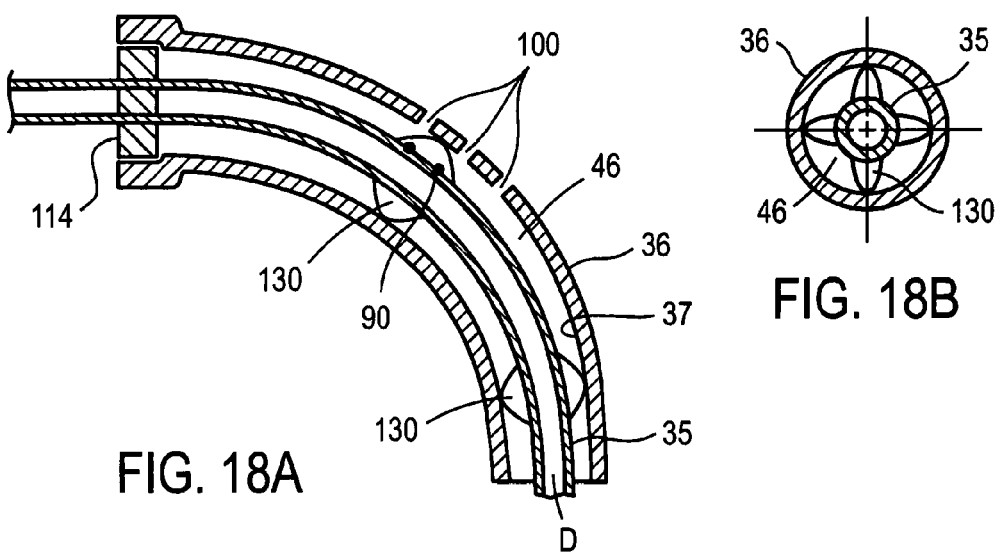
FIG. 18A
FIG. 18B

METHODS AND DEVICES FOR SENSING RESPIRATION AND PROVIDING VENTILATION THERAPY

CROSS-REFERENCE TO RELATED APPLICATIONS

This application is a divisional of U.S. patent application Ser. No. 12/153,423 which claims priority to U.S. Provisional Patent Application Ser. No. 60/924,514, filed May 18, 2007, the disclosure of which is hereby incorporated by reference in its entirety. This application further incorporates by reference in their entireties: U.S. Non-Provisional patent application Ser. No. 10/771,803 (U.S. Pat. No. 7,487,778, issued on Feb. 10, 2009), filed Feb. 4, 2004; U.S. Non-Provisional patent application Ser. No. 10/870,849 (U.S. Pat. No. 7,588,033, issued on Sep. 15, 2009), filed on Jun. 17, 2004, U.S. Non-Provisional patent application Ser. No. 11/523,519 (U.S. Pat. No. 7,533,670 issued on May 19, 2009), filed Sep. 20, 2006 and U.S. Non-Provisional patent application Ser. No. 11/523,518, filed Sep. 20, 2006.

FIELD OF THE INVENTION

The present invention relates to ventilation therapy for persons suffering from respiratory impairment and breathing disorders, such as chronic obstructive pulmonary disease {COPD), pulmonary fibrosis, acute respiratory distress syndrome {ARDS), neuromuscular impairment, sleep apnea and/or other related conditions. More specifically, the present invention relates to accurately and reliably measuring a patient's respiratory pattern using breath sensing, including providing methods, systems and apparatus to protect breath sensors.

STATEMENT RE: FEDERALLY SPONSORED RESEARCH/DEVELOPMENT

Not Applicable

BACKGROUND

There are two general types of control systems for conventional ventilators. A first type is delivery of gas to a patient based on a frequency selected by the clinician. The frequency selected delivery is independent of patient activity. This control system is used when the patient is non-alert, sedated, unresponsive or paralyzed. In this type of system the ventilator is breathing for the patient. A second type of control system is delivery of gas to the patient in response to an inspiratory effort created by the patient. This type of ventilation helps the patient breathe. There are also ventilators and modes of ventilation that combine the two types of control systems.

In the case of a control system that responds to patient breathing effort, breath effort sensors are required to detect inspiration. In basic conventional systems, the breath sensors detect the start of inspiration using a pressure or flow sensor. The inspiratory effort sensor is located somewhere in the path of ventilation gas delivered by a ventilation gas delivery circuit. A ventilation gas delivery circuit is generally defined as the path of respiration gas delivered by a ventilator. The inspiratory effort sensor may be either inside the ventilator, or in the tubing between the ventilator and the patient, including at the patient end of the tubing. Various attempts have been made to place the inspiratory effort sensor(s) inside the patient, or externally attached to the patient to improve breath effort detection and/or improve response time of the ventilator gas delivery.

Pressure or flow sensors within the ventilation gas delivery circuit have successfully been used to detect the start of inspiration to trigger the ventilator to deliver gas to the patient. However, when there is a need or desire to measure the entire respiratory curve in addition to start of inspiration, sensors within the ventilation gas delivery circuit produce inadequate results because the gas being delivered by the ventilator also moves past the sensor. Thus, the sensor no longer measures the patient's respiration, but rather the gas delivered through the ventilation gas circuit. In a closed ventilation system, the ventilator activity approximates the overall lung activity, hence this positioning of sensors may be adequate. In an open ventilation system, or in ventilation systems that augment a patient's spontaneous breathing, sensors within the ventilation gas delivery circuit are inadequate in measuring the entire respiratory curve.

Sensors not within the ventilator gas delivery circuit have the ability to measure the entire respiration activity. For example, chest impedance sensors can be used to measure the entire respiratory curve of a patient and to use that signal to control the ventilator and synchronize the ventilator to the patient's breathing. Although an improvement, this approach has the disadvantage that the chest impedance signal is prone to drift, noise and artifacts caused by patient motion and abdominal movement. In another technology, neural activity related to the respiratory drive is used to measure the respiration of a patient. However, this has the disadvantage that it is invasive and requires electrodes typically placed in the esophagus to detect the neural activity.

U.S. Non-Provisional patent application Ser. No. 10/870,849 (U.S. Printed Publication 2005/0034721), which is incorporated by reference in its entirety above, describes a new form of breath sensing with sensors not within a ventilation gas delivery circuit. The sensors may be located in the airway of a patient, for example, in the patient's trachea, but not within the ventilation gas delivery circuit. In this manner, the gas delivery from the ventilator may not dominate the sensor measurements. This intra-airway sensor may measure naturally inspired gas flow of the patient, naturally exhaled gas flow of the patient, and the effect of the ventilator gas delivery on lung volumes. The sensor may not measure gas flowing in the ventilator delivery circuit as in conventional systems. This breath sensing method may then measure, not just the start of inspiration, but the entire respiratory pattern of the patient. This may be advantageous to optimize the synchrony of the ventilator to the patient's natural breath pattern, so that the patient is comfortable. Also, if the goal is to provide therapy during different portions of the respiratory curve, such as during the middle of inspiration, or during a particular pan of the expiratory phase, then this method may be used to accurately measure the entire respiratory curve. This new breath sensing technology, however, may not be simple or obvious to reduce to practice. Sensors within the airway of the patient are prone to problems stemming from tissue interaction, patient-to-patient variability, variability within a given patient over time, and a variable physiological environment that can not be controlled. For example, debris in the airway may collect on the sensors and may cause signal artifacts and disrupt the sensors' ability to accurately and reliably measure the entire breath curve. Or, the sensor could come into contact with the tracheal wall, which may disrupt the sensors' signal. Alternatively, tracheal movement during breathing can affect the signal.

Need exists for improved breath sensing systems and methods for ensuring reliable and accurate breath measurements.

BRIEF SUMMARY

The present invention may be directed to methods and systems for intra-airway breath sensors, especially those sensors not within a ventilation gas delivery circuit, but exposed to a patient's spontaneous respiration airflow. The present invention is an improvement over existing breath sensing techniques. Further, apparatus and methods for shielding and protecting the intra-airway sensors from disruptions such as contacting tissue or accumulating debris are provided.

One aspect of the invention is directed to a breath sensing and ventilation delivery apparatus comprising: a catheter, one or more intra-airway breath sensors coupled to an outer surface of the catheter, and an airflow permeable protector with a proximal end adapted to be positioned outside a patient and a distal end adapted to be placed in an airway of the patient, wherein the airflow permeable protector at least partially surrounds the catheter such that the airflow permeable protector prevents the one or more intra-airway breath sensors from contacting a tissue and reduces accumulation of debris on the one or more intra-airway breath sensors. The airflow permeable protector may be a tracheostomy tube cannula. The cannula may have one or more fenestrations. The cannula may at least partially surround the catheter forming an annular space between the cannula and the catheter. The airflow permeable protector may be a protective shield. The protective shield may be selected from the group consisting of a shield tapered on at least one end, a shield collapsible against an outer surface of the ventilation catheter, stoma sleeve, and combinations thereof. The one or more intra-airway breath sensors may be selected from the group consisting of thermal sensors, pressure sensors, pressure sensing lumen, gas composition sensors, flow sensors, ultrasonic sensors, resistivity sensors, piezoelectric sensors, light emittance/reflectance sensors, and combinations thereof.

Another aspect of the invention is directed to a breath sensing and ventilation delivery apparatus comprising: a ventilation catheter, a tracheostomy tube cannula with one or more fenestrations, wherein the cannula at least partially surrounds the ventilation catheter to create an annular space between an inner diameter of the cannula and an outer diameter of the ventilation catheter, and one or more intra-airway breath sensors within the annular space between an inner diameter of the cannula and an outer diameter of the ventilation catheter. The ventilation catheter may extend beyond a distal portion of the cannula and into an airway. A positioner may be provided for positioning the ventilation catheter at a predetermined position within the cannula. The positioner may be a basket-type device. The positioner may be a deflector in a wall of the cannula. An anchor may be provided for preventing movement of a distal tip of the ventilation catheter. The one or more fenestrations may be located in a position selected from the group consisting of a superior side of the cannula, an inferior side of the cannula, a lateral side of the outer cannula, and combinations thereof. The one or more intra-airway breath sensors may be selected from the group consisting of thermal sensors, pressure sensors, pressure sensing lumen, tubes with sensing lumen, sensing subassemblies, gas composition sensors, flow sensors, ultrasonic sensors, resistivity sensors, piezoelectric sensors, light emittance/reflectance sensors, and combinations thereof. The one or more intra-airway breath sensors may be multiple elements placed in an array, wherein one element is used as a reference signal. The one or more intra-airway breath sensors may be coupled to the ventilation catheter. The one or more intra-airway breath sensors may be coupled to the cannula. The one or more intra-airway breath sensors may be de-coupled from the ventilation catheter and the cannula. The one or more intra-airway breath sensors may be a sensing lumen not in communication with a ventilation catheter gas delivery circuit, wherein the sensing lumen comprises a sensing element and a port positioned in the annular space and wherein the sensing element is located external to a body and communicating with the sensing lumen. The ventilation catheter may be removable from the cannula. A seal may be provided between the cannula and the ventilation catheter at a location proximal to the one or more intra-airway breath sensors. The ventilation catheter may comprise a moveable connection with the cannula.

Another aspect of the invention includes breath sensing and ventilation delivery apparatus comprising: (a) a tubular member with a proximal end and a distal end, wherein the proximal end is adapted to be positioned outside a patient and the distal end is adapted to be positioned in an airway of the patient, wherein the tubular member includes one or more fenestrations, wherein spontaneous respiration by a patient passes through the one or more fenestrations, (b) one or more intra-airway breath sensors within a lumen of the tubular member, wherein a distal end portion of the tubular member is positioned in the airway such that the one or more intra-airway breath sensors are located within the airway, and wherein the one or more intra-airway breath sensors are exposed to the spontaneous respiration by the patient while within the airway. The one or more fenestrations may be located in a position selected from the group consisting of a superior side of the tubular member, an inferior side of the tubular member, a lateral side of the tubular member, and combinations thereof. The one or more intra-airway breath sensors may be selected from the group consisting of thermal sensors, pressure sensors, pressure sensing lumen, tubes with sensing lumen, sensing subassemblies, gas composition sensors, flow sensors, ultrasonic sensors, resistivity sensors, piezoelectric sensors, light emittance/reflectance sensors, and combinations thereof.

Another aspect of the invention includes a breath sensing and ventilation delivery apparatus comprising: (a) a ventilation catheter for ventilation gas delivery including at least one breath sensing lumen including a breath sensing lumen port, (b) an airflow permeable protector at least partially surrounding a portion of the catheter to protect the at least one breath sensing lumen port, (c) a connection to connect the at least one breath sensing lumen to an external sensor, and further wherein the catheter is configured to be placed into an airway of the patient to position the at least one breath sensing lumen port and permeable protector in the airway, and wherein the at least on breath sensing lumen port is protected by the airflow permeable protector but is exposed to spontaneous airflow in the airway. The airflow permeable protector may comprises one or more fenestrations, which are located in a position selected from the group consisting of a superior side of the airflow permeable protector, an inferior side of the airflow permeable protector, a lateral side of the airflow permeable protector, and combinations thereof. The external sensor is selected from the group consisting of thermal sensors, gas composition sensors, flow sensors, ultrasonic sensors, resistivity sensors, piezoelectric sensors, light emittance/reflectance sensors, and combinations thereof.

Another aspect of the invention includes a breath sensing and ventilation catheter apparatus comprising: a ventilation catheter for ventilation gas delivery, at least one breath sensing lumen port positioned on an outside surface of the ventilation catheter, an airflow permeable shield at least partially surrounding the at least one breath sensing lumen port, and wherein the airflow permeable shield prevents contact of the at least one breath sensing lumen port with tissue and reduces accumulation of debris on the at least one breath sensing lumen port. The airflow permeable shield may be a collapsible basket. The airflow permeable shield may be a cone tapering from a proximal end to a distal end, and wherein the cone further comprises one or more fenestrations. The airflow permeable shield may be a cuff. The airflow permeable shield may be a stoma sleeve. The airflow permeable shield may be collapsible against an outer surface of the ventilation catheter. The at least one breath sensing lumen port may be connected to a sensor external to a patient, the sensor selected from the group consisting of thermal sensors, pressure sensors, gas composition sensors, flow sensors, ultrasonic sensors, resistivity sensors, piezoelectric sensors, light emittance/reflectance sensors, and combinations thereof.

Another aspect of the invention includes a method for breath sensing and ventilation comprising: inserting at least one intra-airway breath sensor into a tubular guide positioned with a proximal end adapted to be outside of the patient and a distal end adapted to be inside an airway of a patient, wherein the at least one intra-airway breath sensor is not located within a ventilator gas flow, and wherein the at least one intra-airway breath sensor is shielded from contacting tissue and from accumulating debris by the tubular guide. The tubular guide may be a tracheostomy tube cannula. The cannula may at least partially surround a ventilation catheter for providing the ventilator gas flow, wherein the cannula forms an annular space between the cannula and the ventilation catheter. The at least one intra-airway breath sensor may be within the annular space. The cannula may have one or more fenestrations. The tubular guide may be a protective shield. The protective shield may be selected from the group consisting of a shield tapered on at least one end, a shield collapsible against an outer surface of the ventilation catheter, stoma sleeve, and combinations thereof. The at least one intra-airway breath sensor may be selected from the group consisting of thermal sensors, pressure sensors, pressure sensing lumen, gas composition sensors, flow sensors, ultrasonic sensors, resistivity sensors, piezoelectric sensors, light emittance/reflectance sensors, and combinations thereof.

Another aspect of the invention relates to a method for breath sensing and ventilation comprising: inserting at least one intra-airway breath sensor in a path of a patient's airway airflow, but not within a ventilation gas delivery circuit, monitoring the patient's airway airflow with the at least one intra-airway breath sensor, operating at least one ventilation gas sensor within a ventilation gas delivery circuit, and monitoring the ventilator gas delivery with the at least one ventilation gas sensor simultaneous with monitoring the patient's airway airflow with the at least one intra-airway breath sensor. The at least one intra-airway breath sensor may be coupled to a ventilation catheter. The at least one intra-airway breath sensor can be at least partially surrounded by a protector. The protector may be a tracheostomy tube cannula. The cannula may comprise one or more fenestrations. The protector may be an airflow permeable shield. The airflow permeable shield may be selected from the group consisting of a basket, a cone, a cuff, a grouping of wires or filaments, a shield tapered on at least one end, a shield collapsible against an outer surface of the ventilation catheter, stoma sleeve, and combinations thereof. The at least one intra-airway breath sensor may be selected from the group consisting of thermal sensors, pressure sensors, pressure sensing lumen, gas composition sensors, flow sensors, ultrasonic sensors, resistivity sensors, piezoelectric sensors, light emittance/reflectance sensors, and combinations thereof.

Another aspect of the invention relates to an apparatus for breath sensing and ventilation comprising: a ventilation catheter for supplying ventilation gas to a patient via a ventilation gas delivery channel in the catheter, a sensing conduit not in communication with the ventilation catheter gas delivery circuit, an opening in the sensing conduit for sensing respiration of the patient through the sensing conduit when the opening is positioned within an airway, and a sensing element communicating with the sensing conduit for sensing respiration of the patient, wherein the sensing element is located external to the patient, and a protector at least partially surrounding the ventilation catheter and sensing conduit opening. The protector may be a tracheostomy tube cannula. The cannula may comprise one or more fenestrations. The sensing element may be selected from the group consisting of: a pressure sensor, a flow sensor, a thermal sensor, or an ultrasonic sensor. The protector may be selected from the group consisting of a basket, a cone, a cuff, a grouping of wires or filaments, a shield tapered on at least one end, a shield collapsible against an outer surface of the ventilation catheter, stoma sleeve, and combinations thereof.

Another aspect of the invention relates to a breath sensing and ventilation delivery apparatus comprising: a ventilation catheter, a tracheostomy tube cannula, wherein the tube cannula at least partially surrounds the ventilation catheter to create an annular space between an inner diameter of the cannula and an outer diameter of the ventilation catheter, and one or more intra-airway breath sensors within the annular space between an inner diameter of the cannula and an outer diameter of the ventilation catheter. The one or more intra-airway breath sensors may be coupled to the ventilation catheter. The one or more intra-airway breath sensors may be coupled to the cannula. The one or more intra-airway breath sensors may be de-coupled from the ventilation catheter and the outer cannula. The at least one intra-airway breath sensor may be selected from the group consisting of thermal sensors, pressure sensors, pressure sensing lumen, gas composition sensors, flow sensors, ultrasonic sensors, resistivity sensors, piezoelectric sensors, light emittance/ reflectance sensors, and combinations thereof.

Another aspect of the invention relates to a breath sensing and ventilation delivery apparatus comprising: (a) a ventilation catheter including a ventilation gas delivery channel and a breath sensing lumen, wherein the breath sensing lumen includes a sensing port, and wherein the ventilation catheter is configured to be placed into the lumen of a tracheostomy tube such that the ventilation catheter is at least partially surrounded by the tracheostomy tube to prevent the sensing port from contacting the tracheal wall; and (b) a breath sensor external to the patient communicating "With the breath sensing lumen. The external breath sensor may be a pressure sensor. The ventilation gas delivery channel may be connected to a flow or pressure sensor external to the patient. The tracheostomy tube may be a cannula of a dual cannula tracheostomy tube. The tracheostomy tube may be a single cannula tube. The ventilation catheter may have a locking connector to connect to the tracheostomy tube. The tracheostomy tube may have a fenestration positioned in the airway. The ventilation catheter may have a centering feature to prevent the sensing port from touching the inner wall of the tracheostomy tube. The sensing port may be positioned at a distance away from the distal end of the ventilation catheter.

Another aspect of the invention is directed to a breath sensing and ventilation delivery apparatus comprising: (a) a ventilation catheter including (i) a ventilation gas delivery channel (ii) a breath sensing lumen including a sensing port, (iii) an airflow permeable shield at least partially surrounding the sensing port; (b) a breath sensor placed external to the patient communicating with the breath sensing lumen, wherein the catheter is configured to be placed into an airway of a patient such that the sensing port and at least a portion of the airflow permeable shield is positioned in the airway of the patient such that the airflow permeable shield prevents the sensing port from contacting the airway wall, and such that the sensing port is exposed to airflow in the airway. The external breath sensor may be a pressure sensor. The ventilation gas delivery channel may be connected to a flow or pressure sensor external to the patient. The sensing port may positioned at a distance away from the distal end of the ventilation catheter. The ventilation catheter may be configured to be placed in through a stoma guide. The airflow permeable shield may be collapsible.

Another aspect relates to a method for breath sensing and ventilation delivery comprising: inserting a one end of a ventilation catheter into a tracheostomy tube of a patient, wherein the ventilation catheter includes a gas delivery channel and a breath sensing lumen and a breath sensing lumen port, and connecting at a second end of the ventilation catheter the gas delivery channel to a ventilation gas source and the breath sensing lumen to a breath sensor element. The step of connecting may include connecting to the external breath sensor that is a pressure sensor. The step of connecting may include connecting the ventilation gas delivery channel to a flow or pressure sensor external to the patient. The ventilation catheter may have a locking connector to the tracheostomy tube. The method may include positioning a fenestration in the tracheostomy tube in the airway. The method may include the step of centering the ventilation catheter using a centering feature on the ventilation catheter to prevent the sensing port from touching the inner wall of the tracheostomy tube. The method may include the step of positioning the sensing port at a distance away from the distal end of the ventilation catheter.

Another aspect of the invention relates to a method for breath sensing and ventilation delivery comprising: inserting a one end of a ventilation catheter through a stoma and into an airway of a patient, wherein the ventilation catheter includes a gas delivery channel a breath sensing lumen and a breath sensing lumen port, and a protective shield at least partially surrounding the catheter section inserted into the airway to prevent the sensing lumen port from contacting the airway wall and connecting, at a second end of the ventilation catheter, the gas delivery channel to a ventilation gas source and the breath sensing lumen to a breath sensor element. The step of connecting may include connecting to the external breath sensor is a pressure sensor. The step of connecting may include connecting the ventilation gas delivery channel to a flow or pressure sensor external to the patient. The method may include step of positioning the sensing port at a distance away from the distal end of the ventilation catheter. The method may include the step of positioning the ventilation catheter through a stoma guide. The step of inserting may include inserting the airflow permeable shield that is collapsible.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 1a shows prior art for breath effort detection by using breath sensors within a ventilator gas delivery circuit.

FIG. 1b shows optional prior art using an ultrasonic flow meter. FIG. 1c shows optional prior art using a rotameter flow meter.

FIG. 16 is a cross section of a ventilation catheter with intra-airway breath sensor protected inside a fenestrated outer cannula with inferior and superior fenestration positions.

FIG. 17 shows a ventilation catheter with an outer cannula with fenestrations on a lateral wall of the outer cannula.

FIG. 18A is a cross section of a ventilation catheter with intra-airway breath sensors protected inside a fenestrated outer cannula, with positioning and anchoring features for the ventilation catheter.

FIG. 18B is an end view of the ventilation catheter shown in FIG. 18A.

FIG. 25B is a cross sectional view of the ventilation catheter shown in FIG. 10a.

DETAILED DESCRIPTION OF THE PREFERRED EMBODIMENTS

Figure 1D:
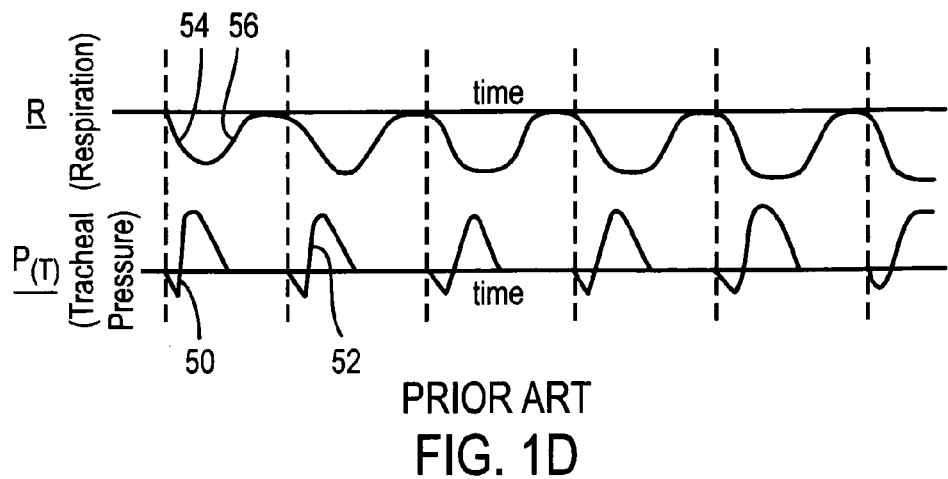
FIG. 1d is a graph illustrating a signal from the system of FIG. 1a where the sensed pressure does not necessarily correspond to respiration.

FIG. 1a shows a prior art ventilator breath detection triggering system where a pressure sensor is located within a ventilation gas delivery circuit 21. A ventilator V may deliver ventilation gas to a patient P through a ventilation gas delivery circuit 21 and a ventilation tube 25. A ventilation circuit pressure tap 22 may be located within the ventilation gas delivery circuit 21. The ventilation circuit pressure tap 22 may sense pressure in the ventilation gas delivery circuit 21. Thus, when the patient P inspires, a negative pressure created in the lung L may be transmitted to the trachea T, and the negative pressure may be detected in the ventilation circuit pressure tap 22. The ventilation circuit pressure tap 22 may be in communication with a ventilator breath delivery control unit 20.

Alternatively, as shown in FIG. 1b, a flow sensor may be used in place of the pressure sensor. The flow sensor may be an ultrasonic flow sensor 30 or another type of flow sensor. Alternatively, as shown in FIG. 1c, a rotameter flow sensor 32 may be located within the ventilation gas delivery circuit 21 to detect inspiration by the patient P, as shown in FIGS. 1a and 1b.

A signal representing the reading from the sensors, which may include, for example but without limitation, a ventilation circuit pressure tap 22, an ultrasonic flow sensor 30, or a rotameter flow sensor 32, may be communicated to the ventilator breath delivery control unit 20 in the ventilator V. The sensors within the ventilation gas delivery circuit 21 may measure the start of a breath. After the ventilator breath delivery unit 20 received the signal, the ventilator V may be triggered to deliver a mechanical breath to the patient P through the ventilation gas delivery circuit 21. After the ventilator V is triggered, the sensors may measure activity of the ventilator V. The sensors may not accurately measure patient breathing.

FIG. 1d shows the measurement of the patient's tracheal pressure P(t) detected by the sensors in comparison with a tracing R of a patient's actual respiration. A patient's inspiration 54 may be initially detected by the sensors as a decrease in pressure from a patient inspiration pressure 50. After triggering of the ventilator V, however, the sensors may only measure ventilator breath delivery pressure 52 and not patient exhalation 56.

Figure 2A:
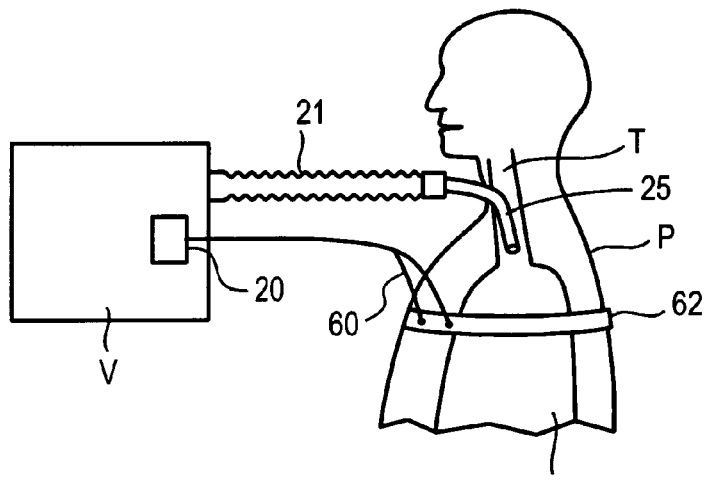
FIG. 2a shows prior art using chest impedance for breath sensing and ventilator control.

FIG. 2a shows a prior art ventilator triggering system where the breath sensor is a chest impedance sensor. The breath sensor is not located within a ventilation gas delivery system 21. A chest impedance sensor may have the drawback that signals representing patient breathing may be affected by motion of the patient P not related to breathing. A chest impedance band 62 may be connected to a ventilator V and corresponding ventilator breath delivery control unit 20 by chest impedance wires 60.

Figure 2B:
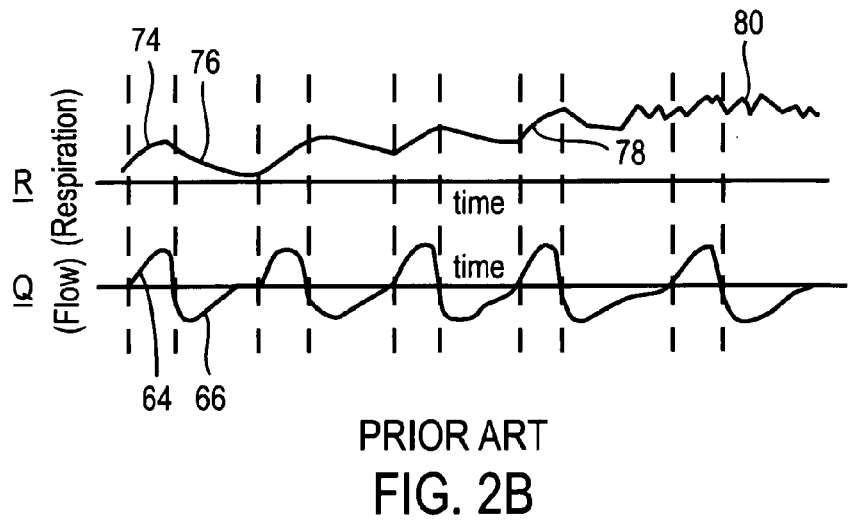
FIG. 2b is a graph illustrating a drift in the impedance signal of FIG. 2a caused by an environmental or stability problem.

FIG. 2b shows a respiration trace R of the patient P, which may correspond to the patient's actual breathing for a certain time, as compared to a flow of gas in a patient's trachea T as shown in tracheal airflow tracing Q. A patient inspiration tracheal flow curve 64 and a patient exhalation tracheal flow curve 66 may be detected by the chest impedance band 62 as seen in a chest impedance inspiration trace 74 and a chest impedance exhalation trace 76, respectively. However, due to motion and patient position and other factors, the chest impedance signal may have chest impedance signal drift 78 or may have chest impedance signal noise from patient motion 80.

Figure 3A:
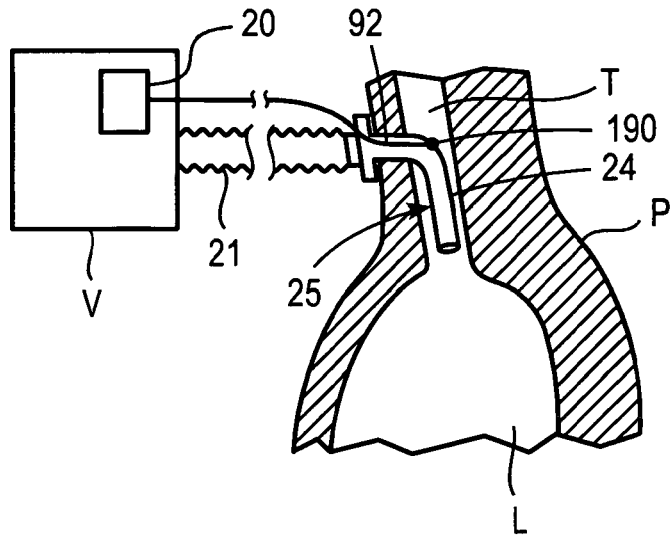
FIG. 3a shows prior an in which intra-airway breath sensors are used for ventilator control and monitoring respiration activity.

FIG. 3a shows a prior art breath sensing system. An intra-airway breath sensor 190 may be located in an airflow path of a patient P in the patient's trachea T.

The intra-airway breath sensor 190 may be used to detect spontaneous breathing by the patient P. To effectively measure spontaneous breathing, the intra-airway breath sensor 190 is preferably not located within a ventilation gas delivery circuit 21. For purposes of this disclosure, a sensor not located within the ventilation gas delivery circuit 21 may be considered to be "in parallel" to the ventilation gas delivery circuit 21. Sensors that are located within the ventilation gas delivery circuit 21 may be considered "in series" in relation to the ventilation gas delivery circuit 21 for purposes of this disclosure. Sensors that are within the ventilation gas delivery circuit 21 may not adequately measure spontaneous breathing after the triggering of a ventilator V because the sensor may then measure primarily the gas delivered by the ventilator V and because the spontaneous breathing may move substantially less air than the ventilator V. A benefit of not having sensors in communication with the ventilator gas delivery circuit is that the sensor may measure the entire spontaneous breathing signal even after triggering the ventilator V because the sensor would not be within the stream of gas supplied by the ventilator V. Sensors outside of the ventilator gas delivery circuit are not directly measuring gas delivered from the ventilator V.

The intra-airway breath sensor 190 of FIG. 3a may not be in communication with the ventilation gas delivery circuit 21. The intra-airway breath sensor 190 may be mounted on an outside surface of ventilation tube 25. The intra-airway breath sensor 190 may measure spontaneous breathing and create a signal representing the spontaneous breathing. The signal may be communicated to a ventilator breath delivery control unit 20 within the ventilator V by intra-airway breath sensing wires 92, wireless technology, RFID, or other communications technology.

The positioning of the intra-airway breath sensor 190 within the trachea T not in communication with a ventilator gas delivery circuit 21 may be an improvement over conventional systems because the intra-airway breath sensor 190 may be less prone to drift and disturbance from environmental influences and patient movement. The sensor may also be less invasive and obtrusive to the patient P, and may be more convenient for a supervising clinician. The intra-airway breath sensor 190 may be mounted on a portion 24 of a ventilation tube 25 inserted into the airway of a patient P. Additionally, when the ventilator V is triggered to deliver gas to the patient P through the ventilation gas delivery circuit 21, a measurement by the intra-airway breath sensor 190 may not be dominated by action of the ventilator V and may continue to measure spontaneous respiration of the patient P.

Figure 3B:
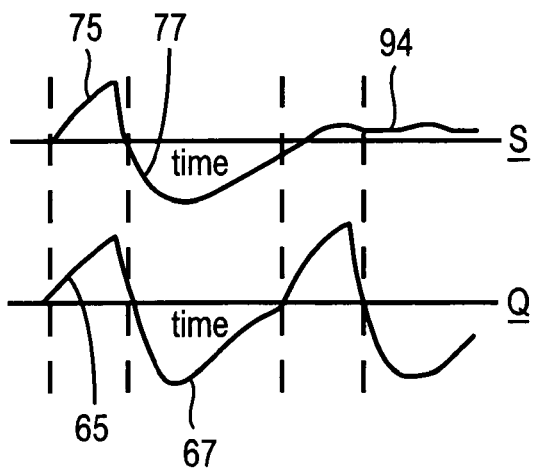
FIG. 3b is a graph illustrating a disruption of the sensor signal of FIG. 3a caused by an environmental problem.

FIG. 3b shows a tracheal airflow trace Q compared with a breath sensor signal tracing S. Patient inspiration tracheal flow 65 and patient exhalation tracheal flow 67 compare well with an inspiration trace 75 and an expiration trace 77, respectively. However, the intra-airway breath sensor 190 may be susceptible to contacting tissue, such as a wall of the trachea T, or accumulation of debris on a surface of the intra-airway breath sensor 190. Contacting tissue and/or accumulation of debris may disrupt measurement from the intra-airway breath sensor 190 as shown by an intra-tracheal breath sensor signal attenuation from tissue contact or debris 94. Protection of the efficacy and accuracy of the intra-airway breath sensor 190 may be important to ensure proper function of a ventilator gas delivery circuit 21.

Figure 4:
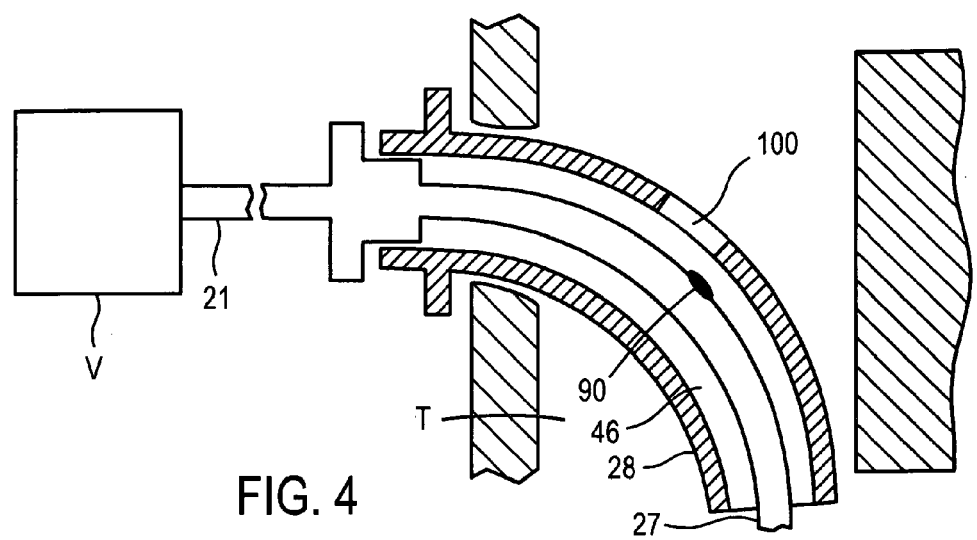
FIG. 4 shows a partial cross-sectional view of the overall system of the invention including a ventilation catheter and a fenestrated outer cannula and a breath sensor in the annular space, and a ventilator.

FIG. 4 shows a system diagram of an embodiment of the present invention. A ventilation catheter 27 may be placed inside an outer tube 28, such as a tracheostomy tube, and a breath sensor or sensors 90 may be placed in an annular space 46 between the ventilation catheter 27 and the outer tube 28 for protection against accumulation of debris and tracheal wall contact. Typically, the system may be configured to facilitate at least part of the patient's spontaneous breathing airflow to travel in the annular space. The sensor signal may be transmitted to the ventilator V to control the ventilator, which may be attached to the ventilation catheter 27 with a gas delivery circuit 21. The outer tube 28 may include fenestrations 100 so gas may flow easily in and out of the annular space 46.

An intra-airway breath sensor 90 may be located in the trachea T, nose, mouth, throat, bronchial or any other location within the path of inhaled and exhaled air. Furthermore, it may be appreciated that embodiments of the present invention may apply to other physiological applications where a catheter is placed in any luminal structure for sensing and therapy. It should be further appreciated that with the appropriate modifications, embodiments of the present invention may be reusable or disposable and may be adapted for adult, pediatric or neonatal use.

The breath sensors in accordance with the principles of the present invention may be thermal sensors, pressure sensors, sensing lumens, gas composition sensors, flow sensors, ultrasonic sensors, resistivity sensors, piezoelectric sensors, light emittance/reflectance sensors, or any other sensor capable of sensing respiration. The breath sensors may be a single sensing element/transducer. Alternatively, the breath sensors may contain multiple sensing elements/transducers for redundancy of signal measurements. Additionally, the breath sensors may contain multiple elements arranged in a sensing array such that at least one of the multiple elements may be used as a reference signal. In the present disclosure, a sensor may be referred to as either singular or plural, however, all of the above configurations may apply.

Figure 5:
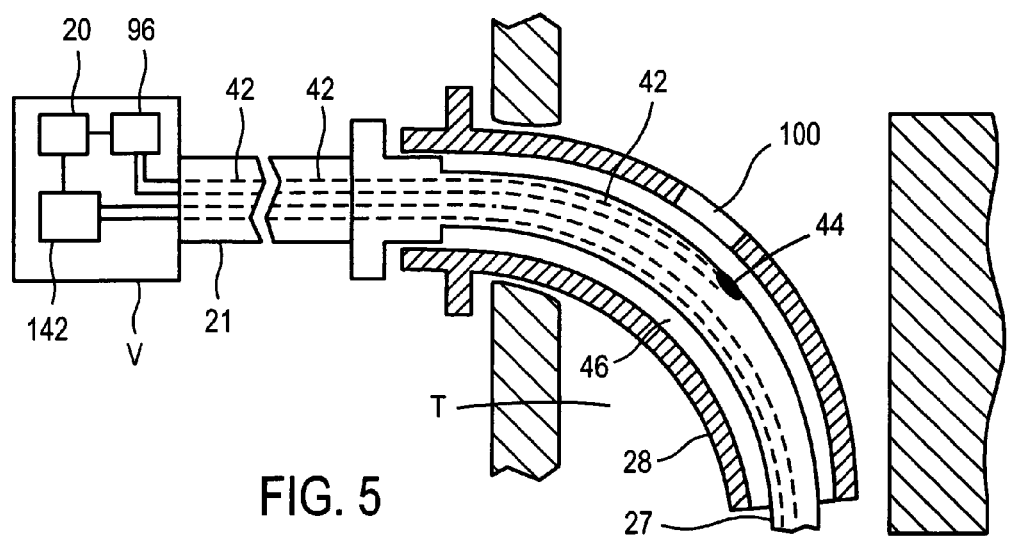
FIG. 5 shows a partial cross-sectional view of the overall system of the invention including a ventilation catheter, a fenestrated outer cannula and a breath sensing lumen and sensing port, and a sensor placed outside the patient in a ventilator

Preferably, the breath sensors may be mounted on a portion of a ventilation tube inserted into the airway of a patient P as shown in FIG. 4 Alternatively, as shown in the system diagram in FIG. 5, an external breath sensor 96 may be positioned outside the body. The external breath sensor 96 may measure airflow or breathing pressure occurring in the patient airway via a sensing conduit or lumen 42. The sensing conduit or lumen 42 may have an opening or sensing port 44 within a patient airway in the annular space 46 between the ventilation tube 27 and the outer tube 28. The conduit or lumen 42 may run from the opening 44 to an external breath sensor, for example a sensor 96, located in the ventilator V. The sensor 96 may communicate with a control unit 20 to control a gas delivery device 142 to control the delivery of gas to the patient.

Fenestrations 100 in the outer tube 28 may be provided as shown in FIGS. 4 and 5 to facilitate spontaneously breathing airflow travels in the annular space. Alternatively, as shown in FIG. 6, the outer tube 28 can be without fenestrations, and the sensor 90 may register the tracheal breathing pressures that are occurring without requiring an open flow path through the outer tube 28.

Figure 6:
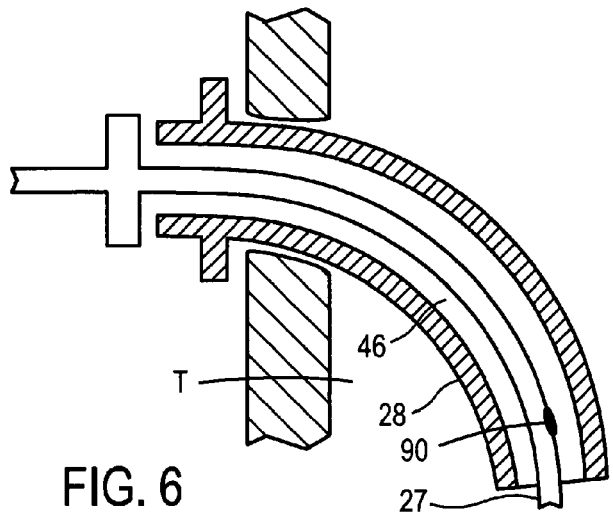
FIG. 6 shows a ventilation catheter and non-fenestrated outer cannula with a breath sensor in the annular space.
Figure 7:
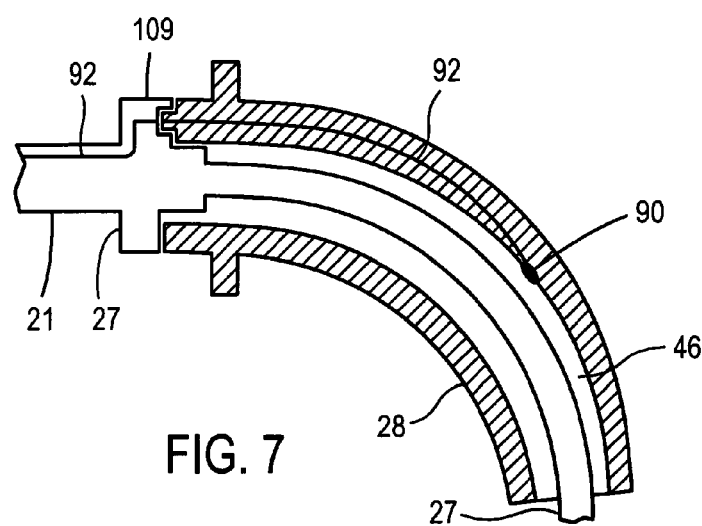
FIG. 7 shows a ventilation catheter and an outer cannula with a breath sensor pan of the outer cannula.

The breath sensor or external breath sensor and corresponding sensing conduit may be coupled to a ventilation tube as shown in FIGS. 4-6. Alternatively, the breath sensor or external breath sensor and corresponding sensing conduit may be integrated with other components of the present invention as described herein. For example, a breath sensor 90 may be part of the inner wall of the outer cannula 28, as shown in FIG. 7. The ventilation catheter 27, when inserted into the outer cannula 28 may form an electrical connection with the sensor 90 so the sensor signal may be transmitted to the ventilator with wiring 92.

Figure 8:
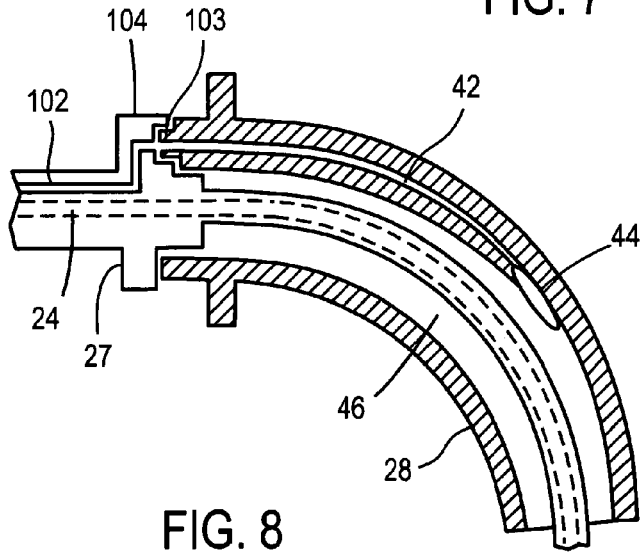
FIG. 8 shows a ventilation catheter and an outer cannula with a breath sensing lumen and port as pan of the outer cannula.

Or, as shown in FIG. 8, a sensing lumen 42 and sensing lumen port 44 can be coupled to the outer cannula 28. When the ventilation catheter 27 is connected to the outer cannula 28, the outer cannula sensing lumen 42 connects via a pneumatic female and male connection 104, 103, respectively, to an external lumen 109 extending away from the patient to an external sensor (not shown), for example, a sensor 96 located in the ventilator V as previously shown in FIG. 5. In FIGS. 7 and 8, the sensor 90 or sensing lumen 42 and port 44 may be located on the superior side of the outer tube 28, in which case fenestrations 102, if present, may be located on lateral walls of the outer tube (described later). Alternatively, the sensor 90 or sensing lumen 42 and port 44 shown in FIGS. 7 and 8 can be located on the inferior side of the outer tube 28, in which case fenestrations may be located on the superior side of the outer tube 28. Further, the sensor 90 or sensing lumen 42 and port 44 can be located on a lateral wall of the outer tube 28.

Figure 9:
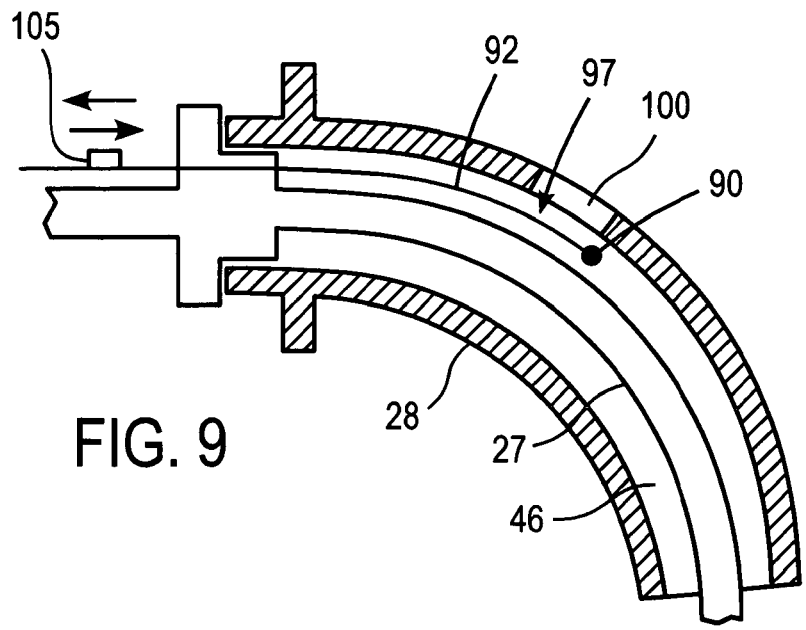
FIG. 9 shows a ventilation catheter and an outer cannula and a separate sensor assembly placed in the space between the ventilation catheter and outer cannula.

Alternatively, the breath sensor or external breath sensor may be decoupled from the various components of the present invention. For example, as shown in FIG. 9, a separate assembly 97 including the sensor 90 can be inserted into the annular space 46 between the ventilation catheter 27 and outer cannula 28. The separate assembly 97 and sensor 90 can be inserted or retracted using a handle 105.

Figure 10:
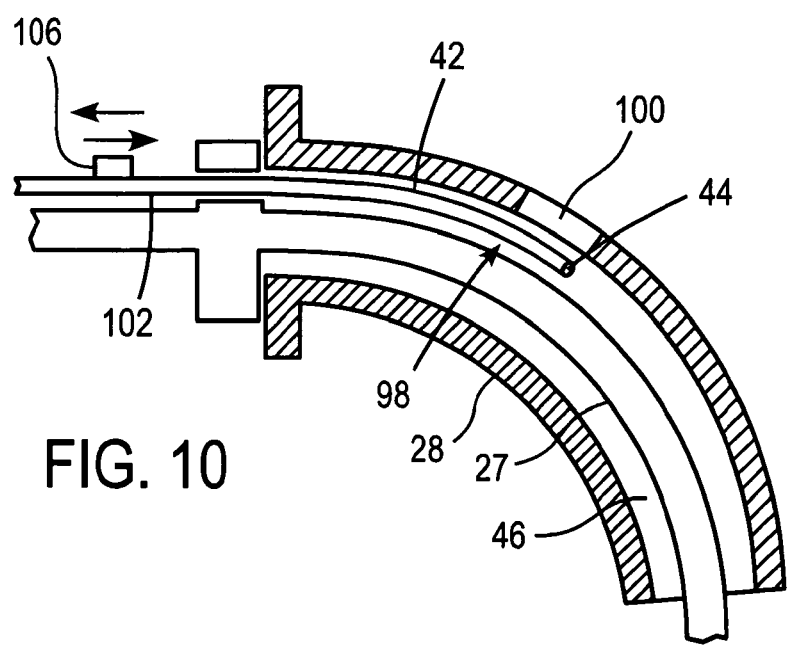
FIG. 10 shows a ventilation catheter and an outer cannula and a separate sensing lumen assembly placed in the space between the ventilation catheter and outer cannula.

Or, alternatively, as shown in FIG. 10, a separate assembly 98 comprising a sensing lumen 42 can be inserted into the annular space 46 between the ventilation catheter 27 and the outer cannula 28, where the sensing lumen 42 connects via an external sensing lumen 109 to sensor positioned outside the body, for example a sensor 96 at the ventilator V as shown in FIG. 5. The separate assembly 98 and sensing lumen 42 can be inserted and retracted using a handle 106.

As described herein, various embodiment of protective configurations, apparatuses and methods for breath sensors may be provided to reduce tissue contact with the breath sensors and accumulation of debris on the breath sensors. The breath sensor may be at least partially surrounded by airflow-permeable coverings, protectors or shields that allow spontaneous respiration to pass through the airflow-permeable coverings and reach the breath sensors. Thus, in accordance with the principles of the invention, various embodiments and configurations described and shown are contemplated and the specific embodiments and configurations are not limiting.

Figure 11:
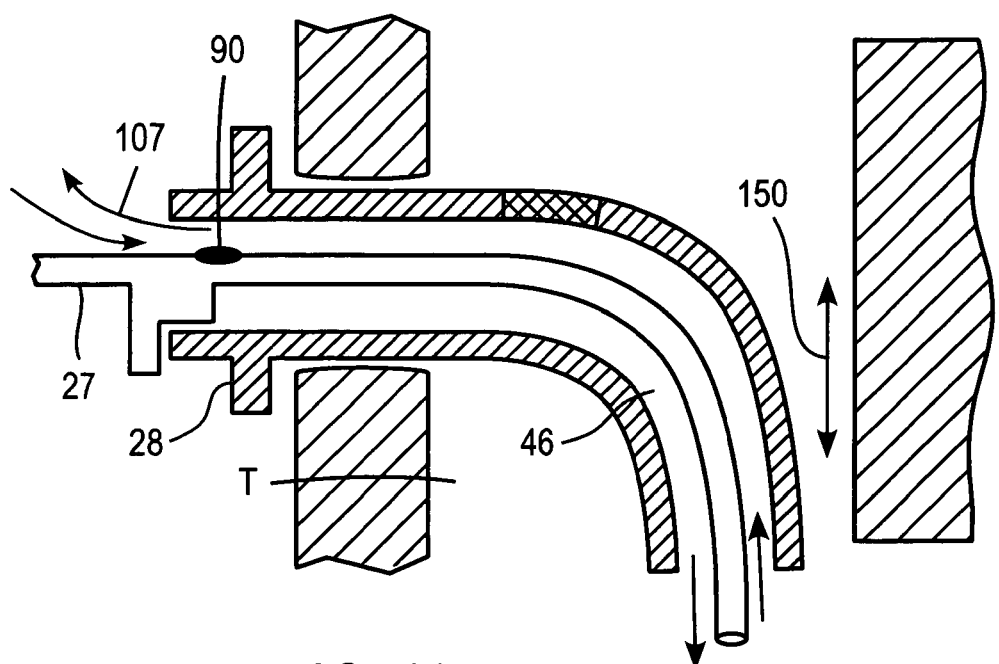
FIG. 11 shows a ventilation catheter and an outer cannula with an channel open to ambient between the catheter and cannula and a sensor in the channel

FIG. 11 shows an alternative where the annular space 46 between the ventilation tube 27 and outer cannula 28 may communicate with ambient air depicted by arrows 107. Some of the spontaneous breathing airflow in the trachea T, indicated by arrow 150, may travel to and from ambient through the annular space 46. The sensor 90 may be placed in the annular space 46 and may register the breathing signal.

Figure 12A:
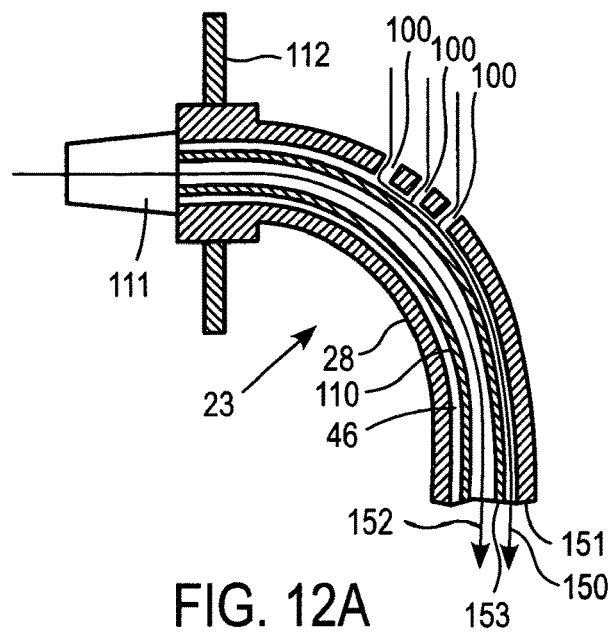
FIG. 12A shows a dual lumen trach tube with fenestrated outer cannula.
Figure 12B:
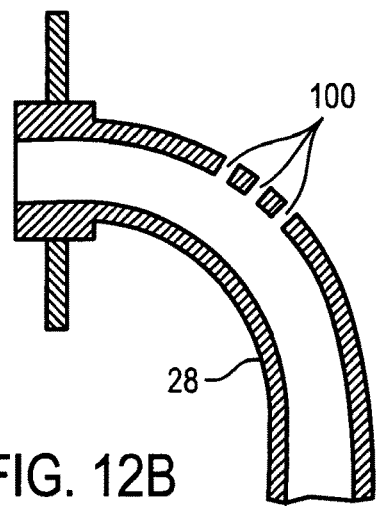
FIG. 12B shows the outer cannula of FIG. 12A with the inner cannula removed.
Figure 12C:
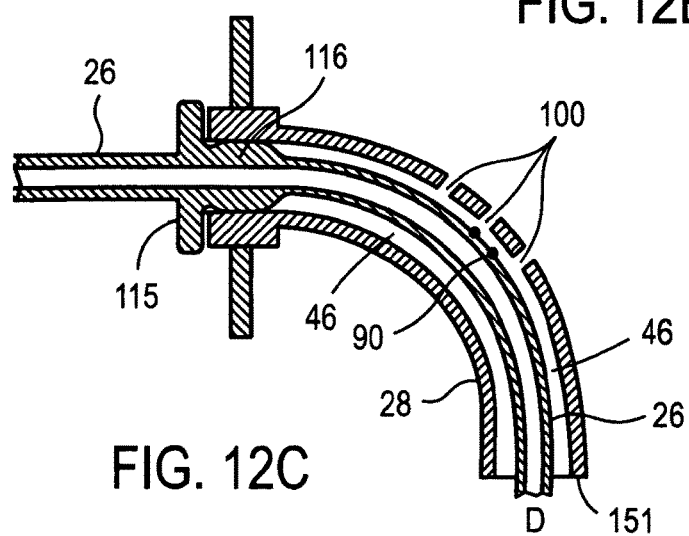
FIG. 12C is a cross section of a ventilation catheter placed inside the fenestrated outer cannula of FIG. 12B where a sensing element is positioned in an annular space.

FIGS. 12A-12C show the sequence of operation and configuration when using a dual cannula tracheostomy tube assembly 23 containing a tracheostomy tube inner cannula 110 and a tracheostomy tube outer cannula 28. For purposes of this invention, the terms ventilation catheter, ventilation tube, and related expressions are used interchangeably. Similarly, the terms tracheostomy tube, outer cannula, outer tube and related expressions are used interchangeably. Various combinations of elements in alternative embodiments may be combined together within the scope of the present invention.

FIG. 12A shows the tracheostomy tube outer cannula 28 surrounding the tracheostomy tube inner cannula 110. The tracheostomy tube outer cannula 28 may be disposed relative to the tracheostomy tube inner cannula 110 such that an annular space 46 may exist between an inner surface of the tracheostomy tube outer cannula 28 and an outer surface of the tracheostomy tube inner cannula 110. The tracheostomy tube outer cannula 28 may have one or more fenestrations 100 to allow airflow into the annular space 46. As indicated by arrows 150, spontaneous respiration may pass through the one or more fenestrations 100 into the annular space 46 and out an end 151 of the tracheostomy tube outer cannula 28. Ventilation gas (arrow 152) from a ventilator may pass through the tracheostomy tube inner cannula 110, out an end 153 of the tracheostomy tube inner cannula 110 and into a patient airway. Ventilation gas (arrow 152) and/or spontaneous respiration 150 may also pass through tracheostomy tube inner cannula 110 and the annular space 46, respectively, in the reverse direction. Fenestrations 100 may permit flow of gas past the dual cannula tracheostomy tube 23 to and from the upper airway. The fenestrations 100 may also permit speech by allowing exhaled air flow past vocal cords.

The dual cannula tracheostomy tube 23 may include a tracheostomy tube neck flange 112 and/or a tracheostomy tube ventilation circuit connector 111. The tracheostomy tube ventilation circuit connector 111 may allow the dual cannula tracheostomy tube 23 to be connected to various types of ventilators. The dual cannula tracheostomy tube 23 configuration may be used when it is preferred to have the option of removing the ventilator and ventilation catheter and allowing the patient to breathe through the outer cannula.

FIG. 12B shows an embodiment of the present invention with the tracheostomy tube inner cannula 110 removed from the tracheostomy tube outer cannula 28 which is left in position in the patient airway.

FIG. 12C shows another variation of an inner cannula ventilation catheter 26 substituted for the tracheostomy tube inner cannula 110. The inner cannula ventilation catheter 26 may be configured to be placed inside the tracheostomy tube outer cannula 28 for precise positioning of intra-airway breath sensors 90 in the annular space 46 between the inner cannula ventilation catheter 26 and the tracheostomy tube outer cannula 28. For example, the precise positioning may include obtaining the correct depth of insertion of the breath sensors relative to the outer cannula length, or the correct circumferential orientation of the sensors in relationship to the outer cannula inner wall, as will be explained later. Thus, the intra-airway breath sensors 90 may be protected within the annular space 46 and may not be susceptible to contacting tissue or accumulating debris. However, the intra-airway breath sensors 90 may be in communication with the spontaneous respiration 150 (shown in FIG. 12A) in the inspiratory and expiratory direction and may detect and measure the breathing pattern of the patient P.

A ventilation catheter seal and connector 116 may connect the inner cannula ventilation catheter 26 to the tracheostomy tube outer cannula 28 for sealing, security and positioning and a flange 115 facilitates insertion and removal of the ventilation catheter 26 from the outer cannula 28. The seal and connector may be, for example, a friction fit seal/connector, a twist and lock seal/connector, or a snap-fit seal/connector, a compressible gasket such as silicone, a line-to-line fit between the mating parts, a mating tapered interface, and/or a slight interference fit with one soft material and an opposing hard material. The location of the intra-airway breath sensors 90 may be anywhere inside the annular space 46, however, preferably the intra-airway breath sensors 90 may be positioned at a location between the fenestrations 100 and the end 151 of the tracheostomy tube outer cannula 28. If the sensors are positioned too close to the distal end of the outer cannula, the sensor may be prone to Venturi artifacts created by gas flow exiting the ventilation catheter from the ventilator. Hence location of the sensors at a distance from the outer cannula opening is preferred.

Because the amount of airflow traveling through the annular space may be only a portion of the total tracheal airflow, the breath signal measured by the breath sensor may be a dampened signal. However, this is deemed acceptable, since the measurement accurately reflects flow or pressure, albeit not necessarily reflective of the true amplitude.

In FIG. 12C, the inner cannula ventilation catheter 26 may include rigidity to prevent unwanted flexure of the inner cannula ventilation catheter 26 that may inadvertently cause the intra-airway breath sensors 90 to contact the outer cannula inner wall.

Figure 13:
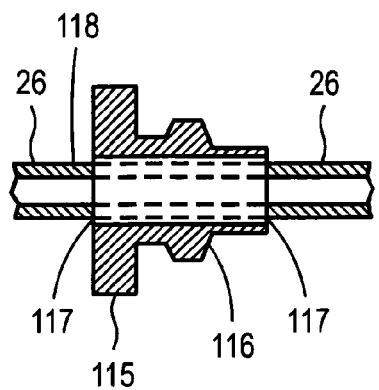
FIG. 13 is a detailed view of an alternative, adjustable ventilation catheter connector.

FIG. 13 shows an alternative connection mechanism where the inner cannula ventilation catheter 26 may include a connector 116 and flange 115 assembly which includes an adjustable sliding seal 117 between the catheter shaft 118 and the connector/flange 116/115 assembly. The ventilation catheter connector/flange assembly 116/115 may be used to position a distal tip D of the inner cannula ventilation catheter 26 and the intra-airway breath sensors 90 in a desired position. The ventilation catheter connector/flange assembly 116/115 may be configured such that it locks or self-locks onto the catheter shaft 118 when not moving the inner cannula ventilation catheter 26. For example, the ventilation catheter connector/flange assembly 116/115 may use a detent system, a collet system, a compression clip a spring-loaded push button, or a locking pin. Alternatively, the position of the intra-airway breath sensors 90 may be adjustable. For example the sensor can be advanced or retracted by moving a rod or wire as shown previously in FIG. 10.

Figure 14:
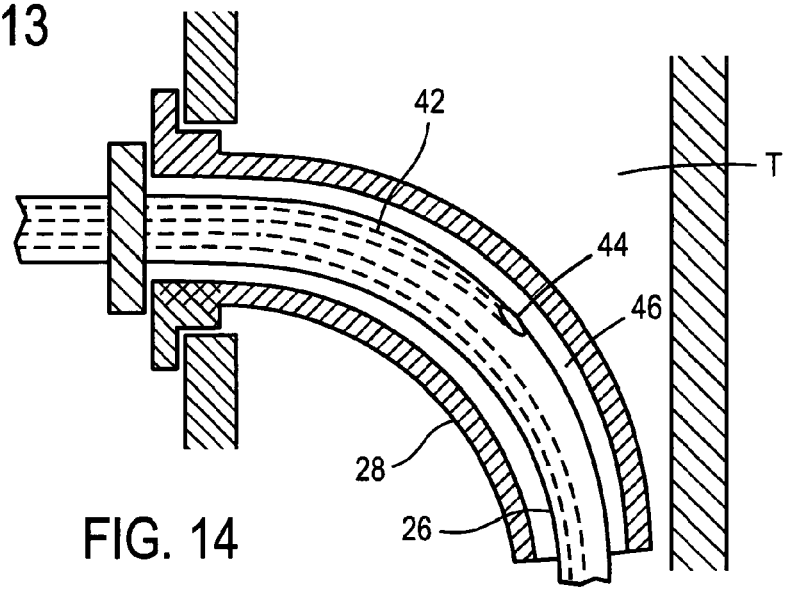
FIG. 14 is a partial cross section of a ventilation catheter placed inside the fenestrated outer cannula of FIG. 12B where a sensing lumen port is positioned in an annular space.

FIG. 14 shows a sensing lumen 42 extending from outside a patient P at a proximal end and into an airway, such as a trachea T. The sensing lumen 42 may have a distal end within the airway with a sensing lumen port/opening 44 positioned in the annular space 46. A sensor may be located outside of the patient P as shown previously in FIG. 5, but may be in communication with the sensing lumen 42, sensing lumen port/opening 44, and/or the airway. This may be advantageous to reduce cost of the ventilation catheter or to reduce the required size of the ventilation catheter.

In addition to the embodiments of FIGS. 12-14, other ventilation catheter and tracheostomy tube combinations and interconnections can be used.

Figure 15:
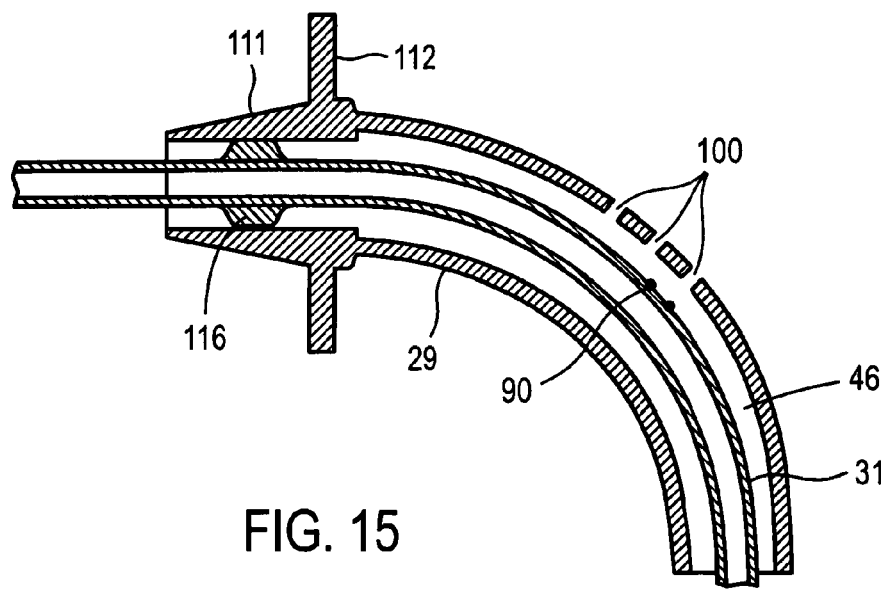
FIG. 15 shows a ventilation catheter with intra-airway breath sensing protected inside a fenestrated single cannula tracheostomy tube.

FIG. 15 describes a ventilation catheter 31 adapted to be inserted into a signal cannula tracheostomy tube 29. The tracheostomy tube 29 may include one or more fenestrations 100 to allow spontaneous respiration to pass between the ventilation catheter 31 and the tracheostomy tube 28. One or more intra-airway breath sensors 90 may be located within the tracheostomy tube 29, or on the ventilation tube 31. The one or more intra-airway breath sensors 90 may be protected within an annular space 46 as previously described. The ventilation catheter 31 and tracheostomy tube 29 may have one or more mating features as those described previously to permit connecting the ventilation catheter 31 and the tracheostomy tube 29. The one or more mating features may position the one or more intra-airway breath sensors 90 in a desired position.

The embodiment of FIG. 15 may also include a tracheostomy tube neck flange 112, a ventilation catheter seal 116 and a tracheostomy tube ventilation circuit connector 111. This embodiment allows the ventilation catheter 31 to be removed and a conventional ventilator and breathing circuit to be connected to the 15 mm connector 111 of the single cannula tracheostomy tube 29, for example, in the event conventional ventilation is required.

Embodiments of the present invention may include various patterns and configurations of fenestrations to allow gas to pass through a sensor protection device onto a sensor. Fenestrations may be located at any location and some preferred locations and configurations are described below. Gas permeable shields for sensors may come in various shapes and numbers, but the gas permeable shields preferably prevent tissue contact with the sensors and/or accumulation of debris on the sensors. For purposes of this invention, the superior direction refers to a position facing an exit of a patient airway from a body of the patient, for example, facing the upper airway. Additionally, the inferior direction refers to a position facing away from the exit of a patient airway from a body of the patient, for example, facing the lower airway. A lateral direction refers to any direction that is not superior or inferior. As discussed above, the fenestrations and/or gas permeable shields may be disposed in any position. The shape of fenestrations may be circular, oval, or any other reasonable shape. The location and shape of the fenestrations can be any combination of the above.

FIG. 16 shows an alternate embodiment of a ventilation catheter 33 and outer cannula tracheostomy tube 34. The outer cannula tracheostomy tube 34 may include one or more fenestrations 100 on a superior side of the tracheostomy tube 120 and/or one or more fenestrations 101 an inferior side of the tracheostomy tube 122. One or more fenestrations 100, 101 on various surfaces of the outer cannula tracheostomy tube 34 may decrease resistance to inspired and expired gas flow through the outer cannula tracheostomy tube 34. Furthermore, one or more fenestrations 100, 101 on various surfaces of the outer cannula tracheostomy tube 34 may provide redundancy for gas flow through the outer tracheostomy tube 34 in the event that one or more fenestrations 100, 101 are miss-aligned, blocked and/or obscured. FIG. 16 also describes an connector/seal 119 that connects to the outer cannula 120.

FIG. 17 shows fenestrations 102 on a lateral sides 121 of the outer cannula tracheostomy tube 34.

Proper positioning of the one or more intra-airway sensors 90 may be important for proper functioning of the breath sensing and ventilator control system. Furthermore, it may be important for the one or more intra-airway sensors 90 to remain in an original or desired position over time. Configurations and methods for positioning and stabilizing the one or more intra-airway sensors 90 may be provided.

FIG. 18A shows an embodiment in which a ventilation catheter 35 includes one or more ventilation catheter stabilization/positioning anchors 130. The one or more ventilation catheter stabilization/positioning anchors 130 may locate and hold one or more intra-airway breath sensors 90 at a desired position within an outer cannula 36. The one or more ventilation catheter stabilization/positioning anchors 130 may help center the ventilation catheter 35 in the outer cannula 36 so the one or more intra-airway breath sensors 90 do not contact an inner wall 37 of the outer cannula 36. The one or more ventilation catheter stabilization/positioning anchors 130 may also prevent the ventilation catheter 35 from whipping when pressurized gas is delivered through the ventilation catheter 35. The one or more ventilation catheter stabilization/positioning anchors 130 may be positioned at one or multiple locations. For example, the one or more ventilation catheter stabilization/positioning anchors 130 may be positioned a location near the one or more intra-airway breath sensors 90 to assure that the one or more intra-airway breath sensors 90 are properly positioned in the annular space 46. Alternatively, the one or more ventilation catheter stabilization/positioning anchors 130 may be positioned a location near a distal tip D of the ventilation catheter 35 to reduce movement of the distal tip during gas delivery. A ventilation catheter outer seal 114 is shown.

FIG. 18B is an end view of FIG. 18A. Other possible configurations of the one or more ventilation catheter stabilization/positioning anchors 130 are possible to locate the one or more intra-airway breath sensors in a desired position within the annular space 46. The anchors are for example compressible filaments or wires, such as an elastomeric filament or a shape memory alloy wire. The filaments or wires can be for example a loop shape, or spokes, or a braid, or a woven basket. The density of the anchor structure is very low offering little to no airflow resistance, unless the anchor is proximal to the fenestration, in which case the anchor can be resistive to airflow since airflow is not needed in that zone for the breath sensors to detect the breathing signal.

Figure 19:
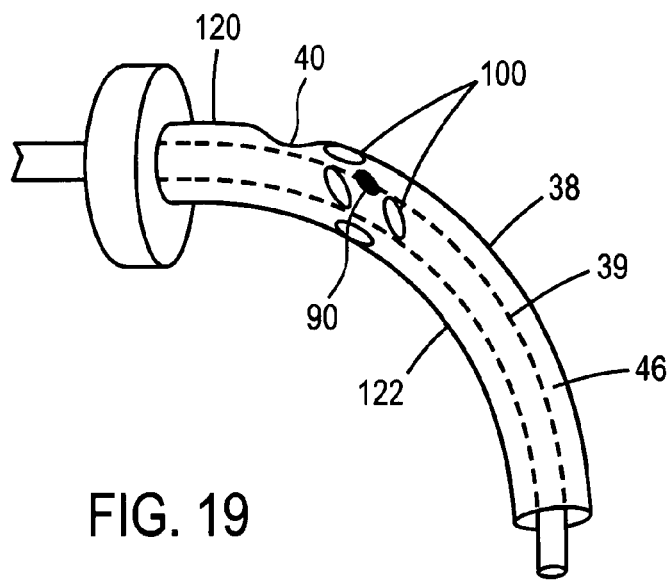
FIG. 19 shows a ventilation catheter with a fenestrated outer cannula having a depression to create an annular gap between the ventilation catheter and the fenestrated outer cannula.

FIG. 19 shows a cannula deflector 40 for ensuring the one or more intra-airway sensors 90 are exposed to air flowing within the annular space 46. The cannula deflector 40 of FIG. 19 is shown in a superior side of the outer cannula 38 for the purpose of spacing a ventilation catheter 39 and sensor 90 away from the inner wall of the outer cannula 38. The ventilation catheter 39 may be formed and shaped into an arc radius that is larger than the arc radius of the outer cannula 38. The cannula deflector 40 may deflect the ventilation catheter 39 into a tighter radius. Therefore, exact matching of the radius of the ventilation catheter 39 to the radius of the outer cannula 38 during manufacturing may be unnecessary. The cannula deflector 40 may be shaped atraumatically to avoid any harsh contact should contact occur between the deflector and the tissue. One or more fenestrations 100 may be positioned at various locations on the outer cannula 38.

Figure 20A:
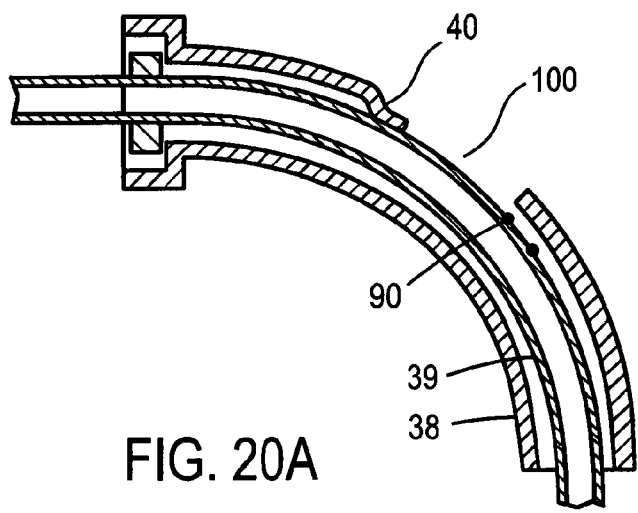
FIG. 20A is a cross section of a ventilation catheter inside a fenestrated outer cannula with a depression adjoining the fenestration in a wall of the outer cannula to create an annular gap between the ventilation catheter and the fenestrated outer cannula.

FIG. 20A shows a cannula deflector 40 in the outer cannula 38 adjoining a fenestration 100. One or more intra-airway breath sensors 90 and/or a sensing lumen port may be positioned just distal to the cannula deflector 40 and the fenestration 100. This may be advantageous when the superior or inferior portion of the cannula which extends into the tracheal lumen from the anterior wall of the trachea, is relatively short, and there is not enough distance between the anterior wall and posterior wall of the trachea for both s deflector and a fenestration if separated from one another.

Figure 21A:
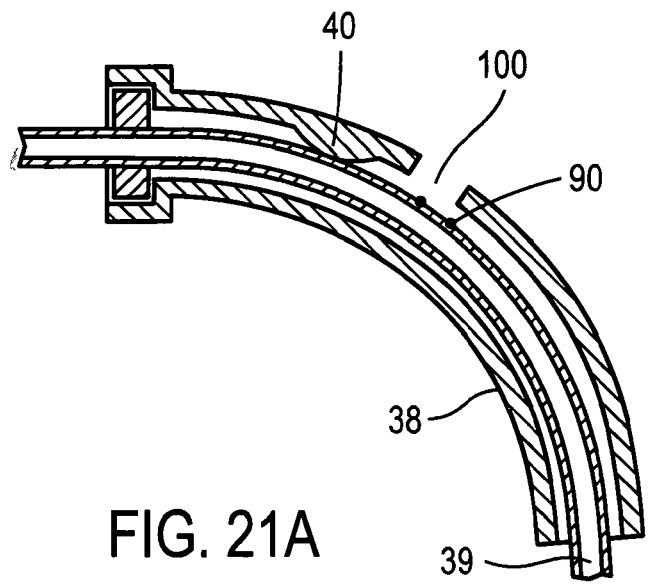
FIG. 21A is a cross section of a ventilation catheter inside a fenestrated outer cannula with a protrusion in an inner wall of the outer cannula to create an annular gap between the ventilation catheter and the fenestrated outer cannula.

FIG. 21A shows a cannula deflector 40 that protrudes only from an inner wall of the outer cannula 38. An outer diameter of the outer cannula 38 may not be affected by the cannula deflector 40. This may be advantageous for insertion and removal of the outer cannula 38 from an airway. The cannula deflector 40 may be near or adjoining one or more fenestration 100 or may be separated from the one or more fenestrations 100 by a predetermined distance. Typically, the deflector and fenestration may have to be located close together due to the limited space requirements imposed by the tracheal diameter. The embodiments described in FIGS. 19, 20A and 21A may be especially applicable in cases in which a single cannula tracheostomy tube is being used, since a tracheostomy tube inner cannula is not placed into the tracheostomy tube. A tracheostomy tube inner cannula, when used with a dual cannula tracheostomy tube, is typically as large as possible to optimize gas delivery. The deflector may require a smaller diameter tracheostomy tube inner cannula contrary to common practice.

Figure 20B:
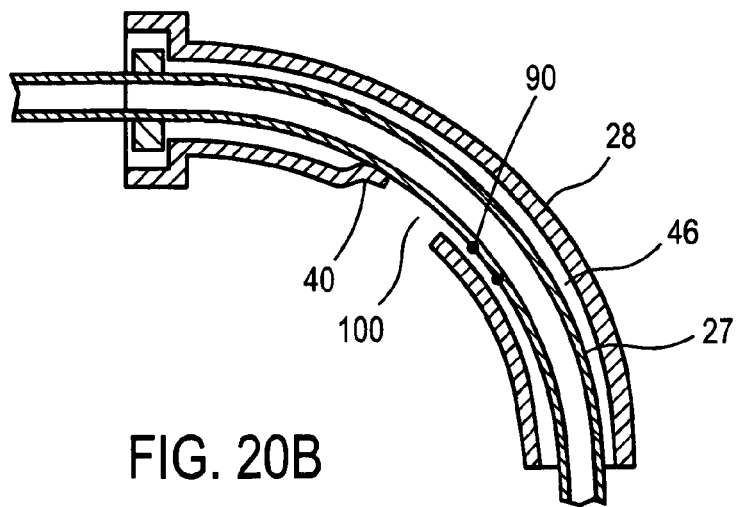
FIG. 20B is a view of the device in FIG. 20A however with the depression on the inferior side.
Figure 21B:
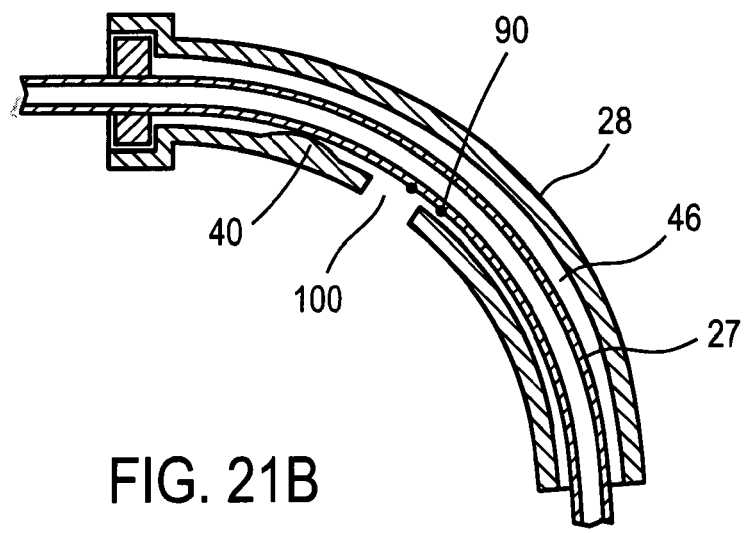
FIG. 21B is a view of the device in FIG. 21A however with the depression on the inferior side.

In addition to the location of the cannula deflector 40 and the one or more intra-airway sensors 90 shown in FIGS. 19, 20A and 21A as a superior location, the cannula deflector 40 may be located at other positions on the outer cannula 38. Other positions for the cannula deflector 40 may be an inferior side 122 of the outer cannula 38 as shown in FIGS. 20B and 21B and/or a lateral side 121 of the outer cannula 38 (not shown). Preferably, the one or more intra-airway sensors 90 may be located on corresponding sides of the ventilation catheter 39. For example, if the cannula deflector 40 is on the inferior side 122 of the outer cannula 38, the one or more intra-airway breath sensors 90 may be located on an inferior side of the ventilation catheter 39. Various positions and combination may be used. The sensor 90 may be positioned at a location away from the midline of the catheter 38 so that when inserted, the sensor does not get damaged by rubbing on the deflector.

Figure 22:
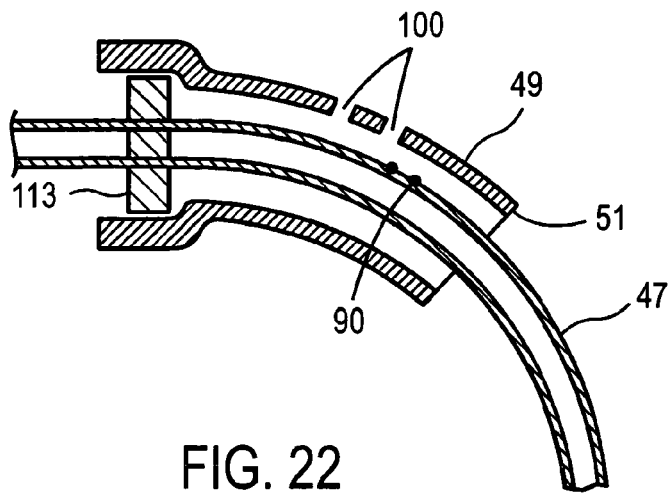
FIG. 22 shows a ventilation catheter with intra-airway breath sensors protected inside a minimally penetrating fenestrated outer cannula.

FIG. 22 shows an embodiment of the present invention with a short tracheostomy tube 49. An inner ventilation catheter 47 may extend distally beyond a distal end 51 the short tracheostomy tube 49. The embodiment of FIG. 8a may be beneficial because the short tracheostomy tube 49 may extend into an airway only as far as necessary to prevent one or more intra-airway breath sensors 90 from contacting the tissue and/or and or reduce accumulation of debris on the one or more intra-airway breath sensors. The patient's airway, therefore, may be potentially more open to spontaneous breathing. In addition, this configuration may facilitate measuring a breathing signal that is closer to the true signal, since there is less obstruction of spontaneous gas flow by the device, for example less Venturi effects, turbulence and dampening of the tracheal flow and pressure. An inner ventilation catheter seal 113 is shown.

Figure 23:
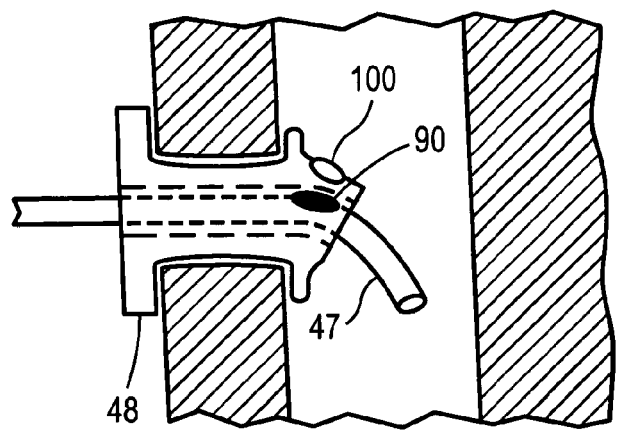
FIG. 23 shows a ventilation catheter inserted through a stoma sleeve where a sensor is protected by a stoma sleeve.

FIG. 23 shows an embodiment of the present invention where the ventilation catheter 47 may be adapted to be placed in a stoma sleeve 48. The stoma sleeve 48 may only marginally extend into the airway. The marginal extension into the airway may provide enough shielding for the one or more intra-airway breath sensors 90 to prevent contact with tissue and/or reduce accumulation of debris. The embodiment of FIG. 22 may be beneficial because the stoma sleeve 48 may be of a relatively small diameter and, therefore, less obtrusive to a patient P. Use of the stoma sleeve 48 may be useful when the patient P is not at risk of requiring full support ventilation because the stoma sleeve 48 typically does not include a standard 15 mm connector required for connection to a conventional ventilator. The stoma sleeve is preferably different than a similar conventional device known as the Montgomery T-Tube, because the stoma sleeve must be configured to create space between the sleeve and the ventilation catheter to define an annular space for the breath sensor. Also, the stoma sleeve is preferably different than a similar conventional device known as a stoma stent such as the Hood Stoma Stent, because the stoma stent does not elongate into the tracheal airway. The stoma sleeve and main lumen there through must elongate a distance into the tracheal lumen in order to define the annular space or protective zone for the breath sensors. Some patients may require the tracheostomy tube compatible version, rather than the stoma sleeve version. For example, if a patient requires other respiratory treatments and accessories on occasion or is at risk of requiring conventional mechanical ventilation, the 15 mm respiratory connector that is part of the tracheostomy tube will facilitate attachment to other respiratory treatments.

Other embodiments of the present invention may have alternative or supplemental protection for the one or more intra-airway breath sensors. For the purposes of this disclosure, the terms protectors and shielding are used interchangeably. Various forms of protection may be used interchangeably or together. In the following exemplary embodiments, the outer cannula or stoma sleeve may be replaced or used with alternative protection devices. Preferably, protectors and/or shields may be airflow permeable.

Figure 24:
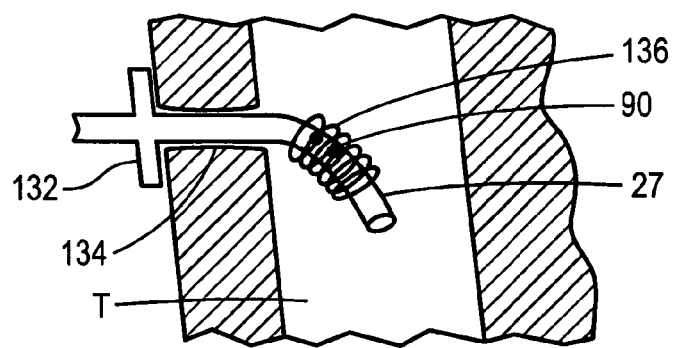
FIG. 24 shows a ventilation catheter with intra-airway breath sensors protected by an air permeable shield that is collapsible.

FIG. 24 shows a fenestrated shield 136 on a ventilation catheter 27. The ventilation catheter 27 may be inserted into an airway, such as a trachea T through a stoma tract 134 or other similar opening. The ventilation catheter may preferably be inserted directly through the stoma tract 134, but may be inserted through a tracheostomy tube or other similar apparatus if needed. A ventilation catheter neck flange 132 may provide positioning and securing of the ventilation catheter 27. One or more intra-airway breath sensors 90 may be mounted on the ventilation catheter 27. The one or more intra-airway breath sensors may be protected by the fenestrated shield 136.

The fenestrated shield 136 may be a basket-type device and is permeable to airflow. The basket may be a woven or braided filament or wire structure with one or both ends of the structure attached to the ventilation catheter shaft. The structure has a normally expanded dimension, but can be easily compressed into a compressed dimension for insertion of the ventilation catheter 27 through the stoma 134.

Figure 25A:
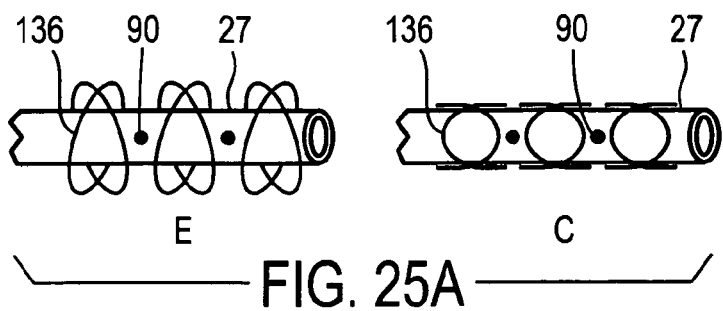
FIG. 25A shows a ventilation catheter with intra-airway breath sensors protected by a permeable wire basket shield that may be collapsible against a catheter shaft and may be expanded when in use.
Figure 25B:
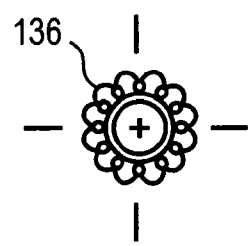

FIG. 25A shows a basket type fenestrated shield 136 that may be collapsed by a pull wire mechanism or stretch mechanism (not shown) from a collapsed state C to an expanded state •E and back The pull wire mechanism is attached to the proximal end of the basket wire structure. Pulling on the wire in the proximal direction elongates the structure proximally, such that the structure diameter reduces or collapses. Therefore, the proximal end of the basket wire structure is slideably attached to the ventilation catheter shaft. The basket type fenestrated shield 136 may also be collapsed by temperature sensitive shape memory alloys that respond to temperature change. The materials may be in a first collapsed state at room temperature, but upon insertion into an airway, the materials may enter a second expanded state based upon the change in temperature from room temperature to the temperature within the airway. The basket type fenestrated shield 136 may also be tapered to facilitate insertion and removal of the ventilation catheter 27 through the stoma. The wires of the basket may be very resilient and pliable to facilitate insertion or removal without requiring uncomfortable amounts of forces. FIG. 25B is an end view of the device of FIG. 25A when in the expanded state. When the basket type fenestrated shield 136 is in an expanded state E, the basket type fenestrated shield 136 has a diameter larger than the diameter of the ventilation catheter 27. However, when the basket type fenestrated shield 136 is in a collapsed state C the basket type fenestrated shield 136 may have a diameter only marginally larger than the diameter of the ventilation catheter 27. In the collapsed state C, the basket type fenestrated shield 136 may collapsed against an outer surface of the ventilation catheter 27.

The one or more intra-airway breath sensors 90 may be disposed on the ventilation catheter 27. Preferably, the basket type fenestrated shield 136 may at least partially surround the one or more intra-airway breath sensors 90 when the basket type fenestrated shield 136 is in an expanded state E. The one or more intra-airway breath sensors 90 may prevent tissue contact and/or may reduce accumulation of debris on the one or more intra-airway breath sensors 90.

Alternatively, the protection device may be a cuff or any other similar structure that is airflow permeable.

Figure 26:
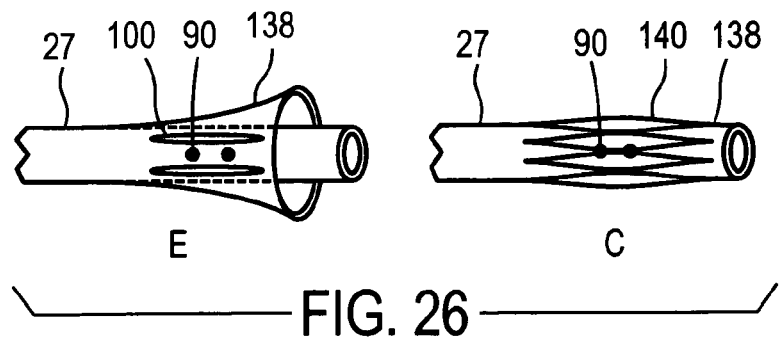
FIG. 26 shows a ventilation catheter with intra-airway breath sensors protected by a permeable conical shield that may be foldable, collapsible against a catheter shaft, and may be expanded when in use.

FIG. 26 shows an airflow permeable shield 138 that may be conical and tapered to favor removal out of a stoma tract 134. The airflow permeable shield 138 may be coupled to a ventilation catheter 27 at a tapered end of the airflow permeable shield 138. The airflow permeable shield 138 may be collapsible. To collapse the airflow permeable shield 138 for insertion, the airflow permeable shield 138 may be composed of shape-memory materials. The airflow permeable shield 138 may be provided in a collapsed state C and then may then expand to an expanded state E after insertion into an airway by responding to body temperature. Alternatively, the airflow permeable shield 138 may be folded by hand or machine into the collapsed state C and then inserted into the airway and then self-expand or manually or mechanically expand to the expanded state E. The airflow permeable shield 138 may assume predetermined conical protective shield folds 140 when collapsed. The airflow permeable shield 138 may manually, mechanically or automatically collapse prior to or during removal from the airway and stoma.

The airflow permeable shield 138 may include one or more fenestrations 100. The one or more fenestrations 100 may be lengthened to facilitate collapsing and expanding of the airflow permeable shield 138. Alternatively, the airflow permeable shield may be permeable to airflow without the one or more fenestrations 100.

Figure 27:
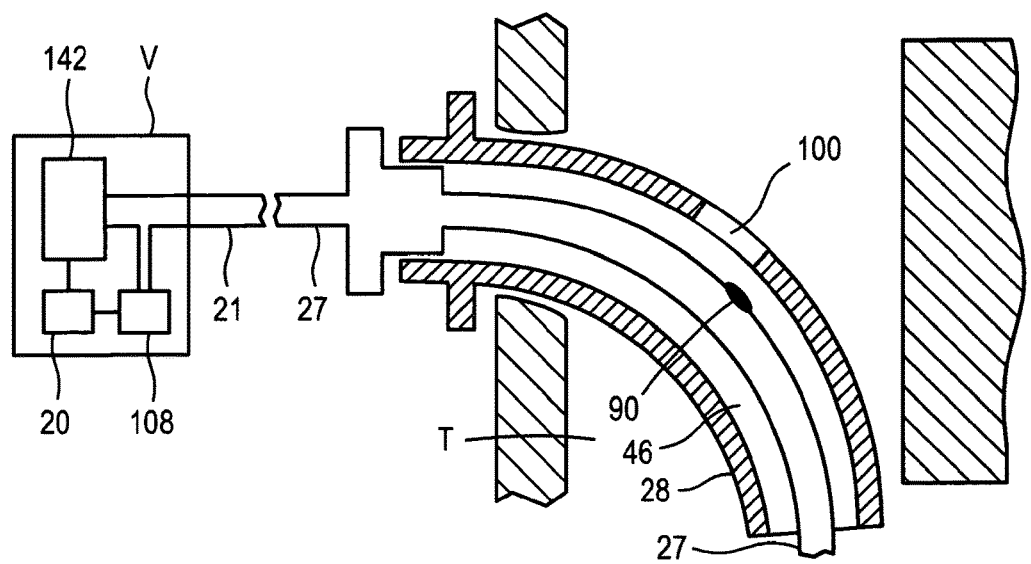
FIG. 27 shows a system layout of the system shown in FIG. 4, with an additional ventilator gas delivery sensor.

The intra-airway breath sensors of various embodiments of the present invention may be combined with breath sensors within the ventilation gas delivery circuit so patient breathing and ventilator activity may be monitored separately, but simultaneously. For example as shown in FIG. 27, the intra-airway breath sensor 90 as described in the above embodiments can be used to measure the patient's breathing, and the effect the ventilator V has on the patient's respiratory system, while a sensor 108 measuring the output of the ventilator V in the gas delivery circuit 21 is measuring the ventilator output.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A breath sensing and ventilation delivery apparatus comprising:
    a ventilation catheter,
    a tracheostomy tube cannula with one or more fenestrations in a wall thereof, wherein the cannula at least partially surrounds the ventilation catheter to create an annular space between an inner diameter of the cannula and an outer diameter of the ventilation catheter, and
    one or more adjustable depth intra-airway breath sensors structurally independent of the ventilation catheter and the tracheostomy tube cannula, and being positionable within the annular space between the inner diameter of the cannula and the outer diameter of the ventilation catheter and within a path of spontaneous patient respiration airflow passing through the one or more fenestrations.

2. The apparatus of claim 1, wherein the ventilation catheter extends beyond a distal portion of the cannula and into an airway.

3. The apparatus of claim 1, further comprising an anchor for preventing movement of a distal tip of the ventilation catheter.

4. The apparatus of claim 1, wherein the one or more fenestrations are located in a position selected from the group consisting of a superior side of the cannula, an inferior side of the cannula, a lateral side of the cannula, and combinations thereof.

5. The apparatus of claim 1, wherein the one or more intra-airway breath sensors are selected from the group consisting of thermal sensors, pressure sensors, pressure sensing lumen, tubes with sensing lumen, sensing subassemblies, gas composition sensors, flow sensors, ultrasonic sensors, resistivity sensors, piezoelectric sensors, light emittance/reflectance sensors, and combinations thereof.

6. The apparatus of claim 1, wherein the one or more intra-airway breath sensors are coupled to the ventilation catheter.

7. The apparatus of claim 1, wherein the ventilation catheter is removable from the cannula.

8. The apparatus of claim 1, further comprising a seal between the cannula and the ventilation catheter at a location proximal to the one or more intra-airway breath sensors.

9. A breath sensing and ventilation delivery apparatus comprising:
(a) a tubular member with a proximal end and a distal end, wherein the proximal end is adapted to be positioned outside a patient and the distal end is adapted to be positioned in an airway of the patient, wherein the tubular member includes one or more fenestrations in a wall thereof, wherein spontaneous respiration by the patient passes through the one or more fenestrations,
(b) one or more adjustable depth intra-airway breath sensors structurally independent of the tubular member and within a lumen of the tubular member,
wherein a distal end portion of the tubular member is positioned in the airway such that the one or more adjustable depth intra-airway breath sensors are located within the airway, and
wherein the one or more adjustable depth intra-airway breath sensors are positioned within a path of the spontaneous respiration by the patient passing through the one or more fenestrations while within the airway.

10. The apparatus of claim 9, wherein the one or more fenestrations are located in a position selected from the group consisting of a superior side of the tubular member, an inferior side of the tubular member, a lateral side of the tubular member, and combinations thereof.

11. The apparatus of claim 9, wherein the one or more intra-airway breath sensors are selected from the group consisting of thermal sensors, pressure sensors, pressure sensing lumen, tubes with sensing lumen, sensing subassemblies, gas composition sensors, flow sensors, ultrasonic sensors, resistivity sensors, piezoelectric sensors, light emittance/reflectance sensors, and combinations thereof.

12. A method for breath sensing and ventilation comprising:
inserting at least one adjustable depth intra-airway breath sensor into a tubular guide positioned with a proximal end adapted to be outside of a patient and a distal end adapted to be inside an airway of the patient, the at least one intra-airway breath sensor being structurally independent of the tubular guide and being positionable within the tubular guide within a path of airflow from spontaneous patient respiration; and
monitoring the patient's airway airflow with the at least one intra-airway breath sensor during ventilation,
wherein, during said monitoring, the at least one adjustable depth intra-airway breath sensor is not located within a ventilator gas flow, and
wherein, during said monitoring, the at least one adjustable depth intra-airway breath sensor is shielded from contacting tissue and from accumulating debris by the tubular guide.

13. The method of claim 12, wherein the tubular guide is a tracheostomy tube cannula.

14. The method of claim 13, wherein the cannula at least partially surrounds a ventilation catheter for providing the ventilator gas flow, wherein the cannula forms an annular space between the cannula and the ventilation catheter.

15. The method of claim 14, wherein the at least one intra-airway breath sensor is within the annular space.

16. The method of claim 13, wherein the cannula has one or more fenestrations.

17. The method of claim 12, wherein the tubular guide is a protective shield.

18. The method of claim 17, wherein the protective shield is selected from the group consisting of a shield tapered on at least one end, a shield collapsible against an outer surface of a ventilation catheter, stoma sleeve, and combinations thereof.

19. The method of claim 12, wherein the at least one intra-airway breath sensor is selected from the group consisting of thermal sensors, pressure sensors, pressure sensing lumen, gas composition sensors, flow sensors, ultrasonic sensors, resistivity sensors, piezoelectric sensors, light emittance/reflectance sensors, and combinations thereof.

* * * * *